US012702841B2

(12) United States Patent
Anastassiou et al.

(10) Patent No.: US 12,702,841 B2
(45) Date of Patent: Aug. 11, 2026

(54) ELECTRICAL STIMULATION ENTRAINMENT OF TARGETED NEURONAL CELL TYPES

(71) Applicant: Allen Institute, Seattle, WA (US)

(72) Inventors: Constantinos Anastassiou, Seattle, WA (US); Soo Yeun Lee, Seattle, WA (US)

(73) Assignee: Allen Institute, Seattle, WA (US)

( * ) Notice: Subject to any disclaimer, the term of this patent is extended or adjusted under 35 U.S.C. 154(b) by 438 days.

(21) Appl. No.: 18/255,813

(22) PCT Filed: Dec. 2, 2021

(86) PCT No.: PCT/US2021/061592
§ 371 (c)(1),
(2) Date: Jun. 2, 2023

(87) PCT Pub. No.: WO2022/120035
PCT Pub. Date: Jun. 9, 2022

(65) Prior Publication Data

US 2024/0100344 A1 Mar. 28, 2024

Related U.S. Application Data

(60) Provisional application No. 63/120,587, filed on Dec. 2, 2020.

(51) Int. Cl.
*A61N 1/36* (2006.01)
*A61N 1/05* (2006.01)

(52) U.S. Cl.
CPC ....... *A61N 1/36171* (2013.01); *A61N 1/0531* (2013.01)

(58) Field of Classification Search
None
See application file for complete search history.

(56) References Cited

U.S. PATENT DOCUMENTS

| | | |
|---|---|---|
| 4,856,526 A | 8/1989 | Liss |
| 8,112,154 B2 | 2/2012 | Rezai et al. |

(Continued)

FOREIGN PATENT DOCUMENTS

| | | |
|---|---|---|
| EP | 2651504 B1 | 10/2013 |
| JP | 2017000835 | 1/2017 |

(Continued)

OTHER PUBLICATIONS

Anastassiou, et al., "Ephaptic coupling of cortical neurons," Nat. Neurosci., vol. 14, No. 2, 2011, pp. 217-223.

(Continued)

*Primary Examiner* — Michael W Kahelin
(74) *Attorney, Agent, or Firm* — C. Rachal Winger; Chrystal Quisenberry; Lee & Hayes PC

(57) ABSTRACT

Electrostimulating waveforms offering simultaneous and controllable cell-type-specific entrainment are described. The waveforms selectively entrain excitatory versus inhibitory cortical and hippocampal neurons including pyramidal neurons, parvalbumin neurons, and somatostatin neurons. The embodiment provides targeted electrical stimulation (ES) entrainment of excitatory versus inhibitory neurons. For example, the current disclosure provides methods of selectively entraining excitatory neurons with ES frequencies below 30 Hertz (Hz) and in particular embodiments to frequencies below 15 Hz, such as 8 Hz and 4 Hz. The current disclosure also provides methods of selectively entraining inhibitory neurons to ES frequencies of at least 30 Hz and depending on the type of inhibitory neuron, utilizing a frequency that is 30-60 Hz or a frequency that is greater than 100 Hz.

20 Claims, 28 Drawing Sheets control (no ES) 8 Hz ES
$V_e$
$V_i$ (Pyr)
0.5 s control (no ES) 140 Hz ES
$V_e$
1 mV
$V_i$ (Pvalb)
30 mV
50 ms

(56) References Cited

U.S. PATENT DOCUMENTS

| | | | | |
|---|---|---|---|---|
| 8,543,219 | B2 | 9/2013 | Tass | |
| 8,554,324 | B2 | 10/2013 | Brocke | |
| 8,880,173 | B2 | 11/2014 | DiUbaldi | |
| 8,948,875 | B2 | 2/2015 | Paulus | |
| 9,211,408 | B2 | 12/2015 | Machado | |
| 9,878,161 | B2 | 1/2018 | Wu et al. | |
| 2006/0173510 | A1 | 8/2006 | Besio et al. | |
| 2009/0082691 | A1 | 3/2009 | Denison | |
| 2011/0307029 | A1 | 12/2011 | Hargrove | |
| 2012/0083861 | A1 | 4/2012 | Fried et al. | |
| 2012/0109241 | A1 | 5/2012 | Rauscher | |
| 2015/0005840 | A1 | 1/2015 | Pal et al. | |
| 2015/0051166 | A1 | 2/2015 | Ziburkus et al. | |
| 2016/0175589 | A1* | 6/2016 | Wingeier | A61B 5/4836 607/45 |
| 2017/0216594 | A1* | 8/2017 | Grossman | A61N 1/0529 |
| 2019/0117980 | A1* | 4/2019 | Benquet | A61N 1/36175 |
| 2019/0160294 | A1 | 5/2019 | Peterson et al. | |
| 2020/0179688 | A1 | 6/2020 | Su | |
| 2022/0126055 | A1* | 4/2022 | Hubbard, Jr. | A61M 21/00 |

FOREIGN PATENT DOCUMENTS

| | | | | |
|---|---|---|---|---|
| WO | WO-2019161034 | A1 * | 8/2019 | A61N 1/36025 |
| WO | WO2019182632 | A1 | 9/2019 | |

OTHER PUBLICATIONS

Bennett, et al,. "Higher-Order Thalamic Circuits Channel Parallel Streams of Visual Information in Mice," Neuron, vol. 102, No. 2, 2019, pp. 477-492.

Denman and Reid, "Synergistic population encoding and precise coordinated variability across interlaminar ensembles in the early visual system," bioRxiv, 2019, 24 pages.

Duvernoy, et al., "The Human Hippocampus: Functional Anatomy, Vascularization and Serial Sections with MRI, 3rd edition," AJNR, vol. 26, No. 10, 2005, 1 page.

Gouwens, et al., "Toward an integrated classification of neuronal cell types: morphoelectric and transcriptomic characterization of individual GABAergic cortical neurons," bioRxiv, 2020, 50 pages.

Histed, et al., "Direct Activation of Sparse, Distributed Populations of Cortical Neurons by Electrical Microstimulation," Neuron, vol. 63, No. 4, 2009, pp. 508-522.

Jia, et al., "High-density extracellular probes reveal dendritic backpropagation and facilitate neuron classification," J. Neurophysiol., vol. 121, 2019, pp. 1831-1847.

Jun, et al., "Fully Integrated Silicon Probes for High-Density Recording of Neural Activity," Nature., vol. 551, No. 7679, 2017, pp. 232-236.

Mitchell, et al., "Differential Attention-Dependent Response Modulation across Cell Classes in Macaque Visual Area V4," Neuron, vol. 55, No. 1, 2007, pp. 131-141.

Negahbani, et al., "Transcranial Alternating Current Stimulation (tACS) Entrains Alpha Oscillations by Preferential Phase Synchronization of Fast-Spiking Cortical Neurons to Stimulation Waveform," bioRxiv, 2019, 44 pages.

Niell and Stryker, "Highly Selective Receptive Fields in Mouse Visual Cortex," J. of Neurosci., vol. 28, No. 30, 2008, pp. 7520-7536.

Search Report and Written Opinion Dated Feb. 25, 2022 for International Application No. PCT/US2021/061592, 16 pages.

Siegle, et al., "A survey of spiking activity reveals a functional hierarchy of mouse corticothalamic visual areas," bioRxiv., 2019, 53 pages.

Tasic, et al., "Shared and distinct transcriptomic cell types across neocortical areas," Nature, vol. 563, No. 72-78, 2018, 41 pages.

Teeters, et al., "Neurodata Without Borders: Creating a Common Data Format for Neurophysiology," Neuron, vol. 88, No. 4, 2015, pp. 629-634.

Valverde, et al., "Deep brain stimulation-guided optogenetic rescue of parkinsonian symptoms," Nature Communications, vol. 11, 2020, 2388.

Wei, et al., "In vivo cortical circuit characterization in a large-animal model through massively parallel extracellular Neuropixels recordings," Program No. 252.17. 2019 Neuroscience Meeting Planner. Chicago, IL: Society for Neuroscience, 2019. Online).

* cited by examiner

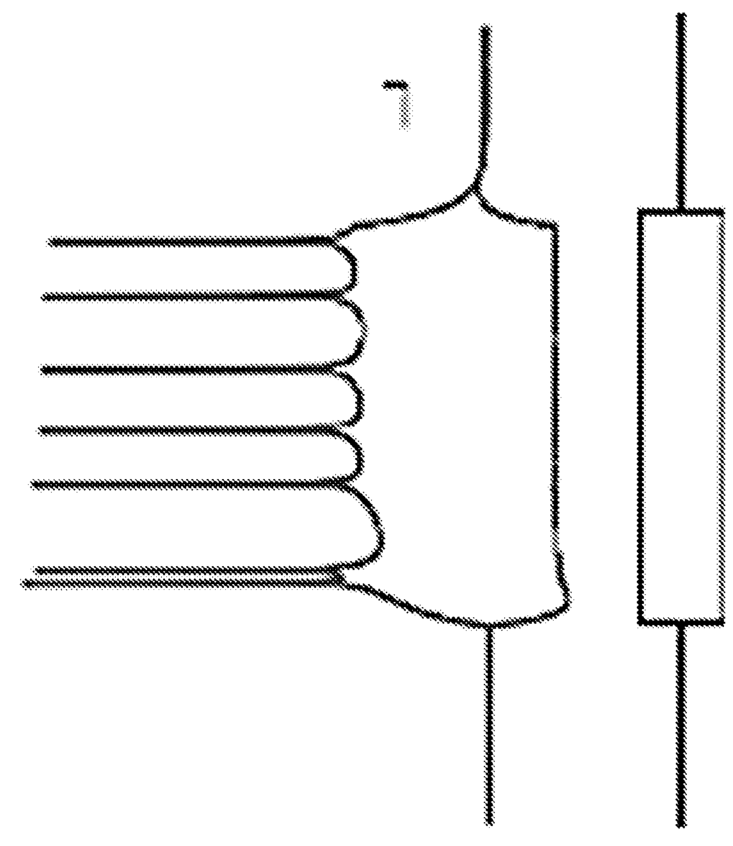
FIG. 5A
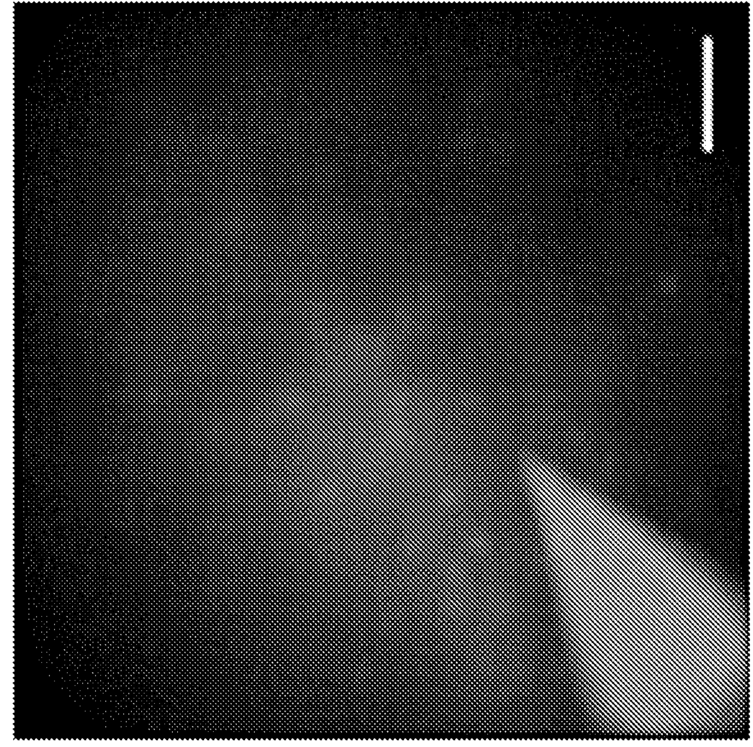

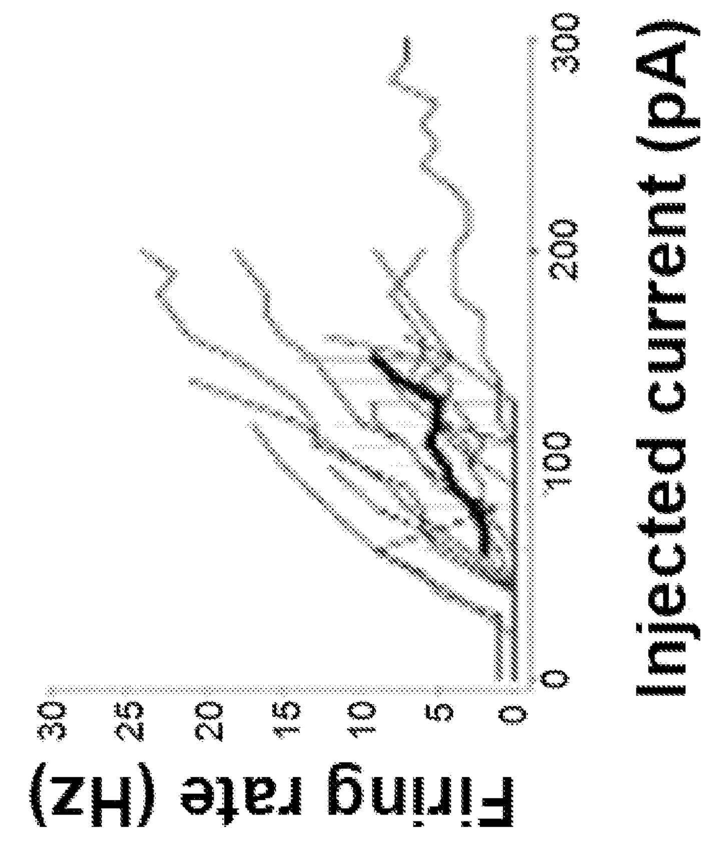
FIG. 5A cont'd.
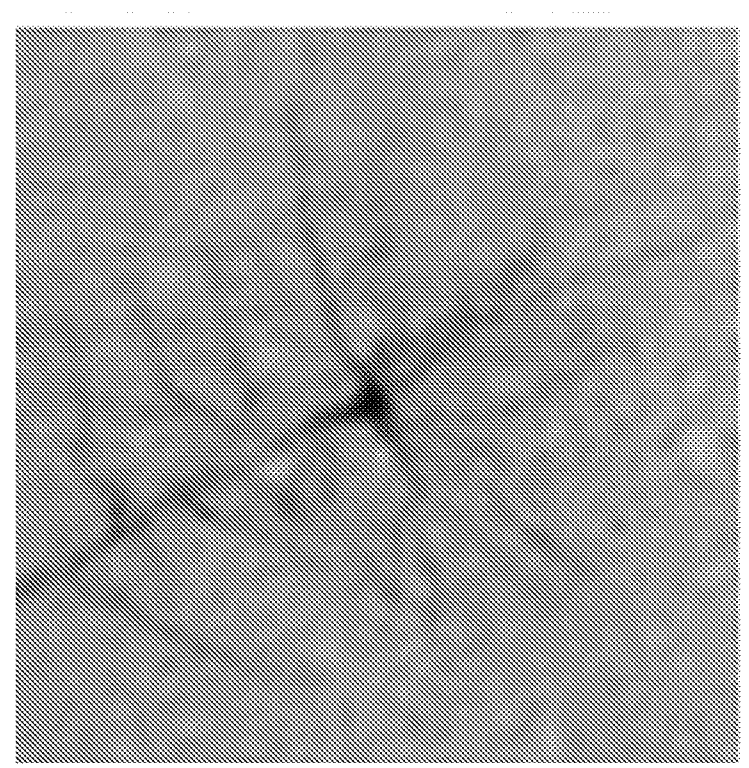

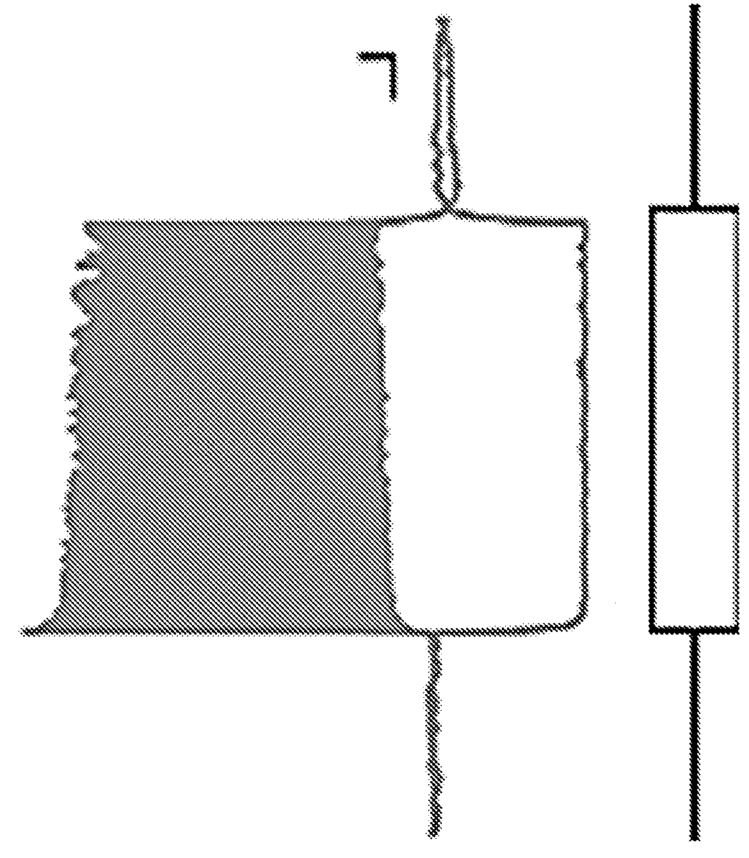
FIG. 5B
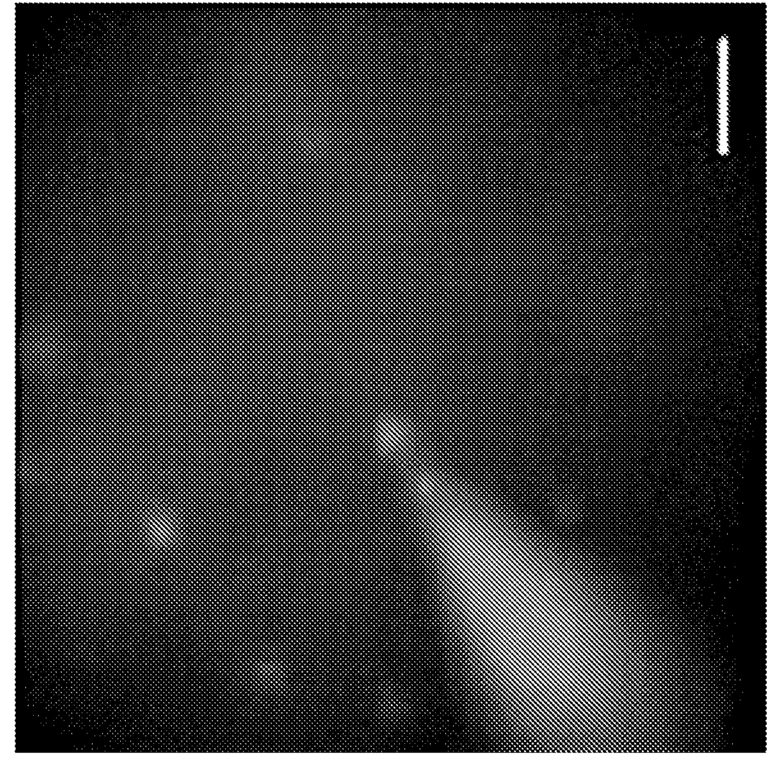

Hippocampus (CA1) Pvalb

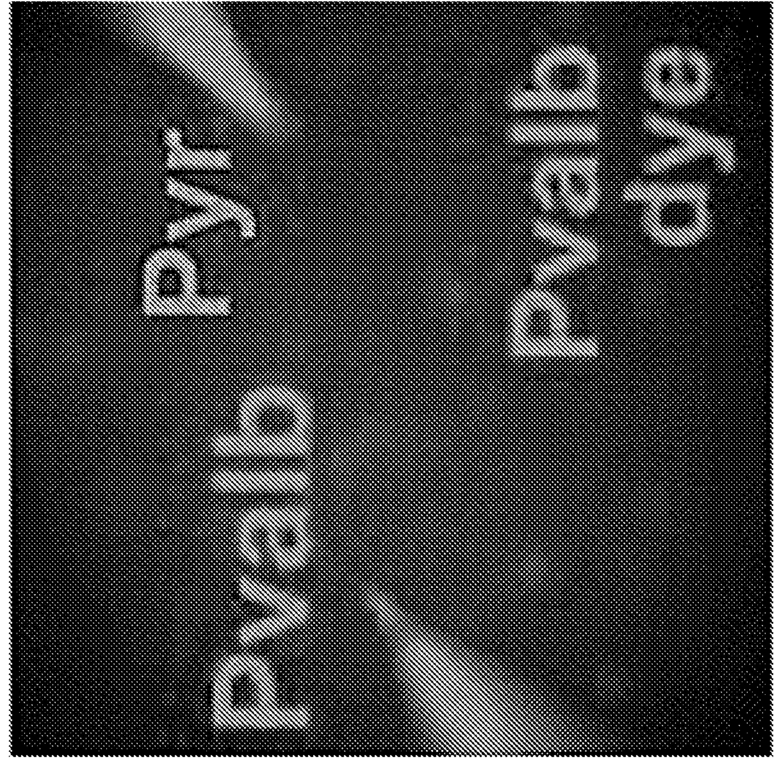
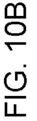
FIG. 10B
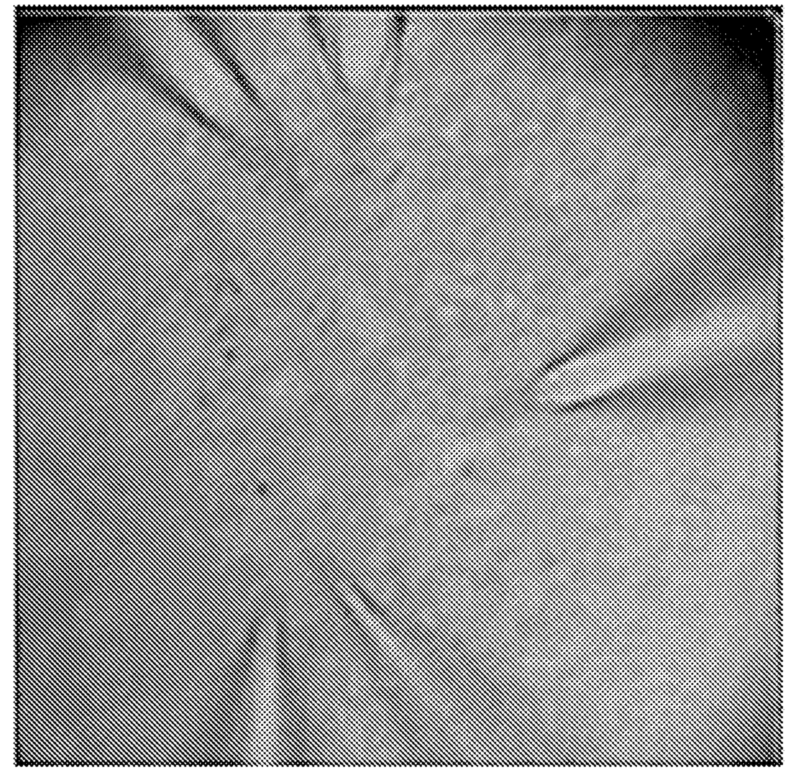

ELECTRICAL STIMULATION ENTRAINMENT OF TARGETED NEURONAL CELL TYPES

CROSS-REFERENCE TO RELATED APPLICATIONS

This application is a U.S. National Phase Application based on International Patent Application No. PCT/US2021/061592, filed on Dec. 2, 2021, which claims the benefit of U.S. Provisional Patent Application No. 63/120,587 filed Dec. 2, 2020, the entire contents of which are incorporated by reference herein.

FIELD OF THE DISCLOSURE

Electrostimulating waveforms offering simultaneous and controllable cell-type-specific entrainment are described. The waveforms selectively entrain excitatory versus inhibitory cortical and hippocampal neurons including pyramidal neurons, parvalbumin neurons, and somatostatin neurons.

BACKGROUND OF THE DISCLOSURE

Electrical stimulation (ES) has been utilized in research and therapeutic approaches, for example, as a means to intervene with pathological activity in neurological disorders such as epilepsy, dementia, and Parkinson's disease. Currently, many ES protocols are applied to the brain without consideration for the remarkable diversity of cell types comprising neural circuits. The ability to more precisely control the effects of ES would provide a significant advance.

SUMMARY OF THE DISCLOSURE

The current disclosure provides targeted electrical stimulation (ES) entrainment of excitatory versus inhibitory neurons. For example, the current disclosure provides methods of selectively entraining excitatory neurons with ES frequencies below 30 Hertz (Hz) and in particular embodiments to frequencies below 15 Hz, such as 8 Hz and 4 Hz. The current disclosure also provides methods of selectively entraining inhibitory neurons to ES frequencies of at least 30 Hz and depending on the type of inhibitory neuron, utilizing a frequency that is 30-60 Hz or a frequency that is greater than 100 Hz.

In particular embodiments, the entrained neurons are within the cortex or the hippocampus. In more particular embodiments, the entrained neurons are within the visual cortex (e.g., the primary visual cortex) or the CA1 region of the hippocampus.

Particular embodiments include entraining excitatory cortical or hippocampal neurons with a sinusoidal waveform having a frequency that is below 30 Hz. Particular embodiments include entraining pyramidal neurons within the cortex with a sinusoidal waveform having a frequency of 4-12 Hz. Particular embodiments include entraining pyramidal neurons within the hippocampus with a sinusoidal waveform having a frequency of 4 Hz.

Particular embodiments include entraining inhibitory cortical or hippocampal neurons with a sinusoidal waveform having a frequency that is 30 Hz or greater. Particular embodiments include entraining parvalbumin (Pvalb) neurons within the cortex or hippocampus with a sinusoidal waveform having a frequency that is greater than 100 Hz. Particular embodiments include entraining somatostatin (SST) neurons within the cortex or hippocampus with a sinusoidal waveform having a frequency that is 30 Hz-60 Hz.

Particular embodiments provide composite waveforms to entrain an excitatory or inhibitory neuron as described above with another selected cell type. Composite waveforms can also be generated to entrain a combination of excitatory or inhibitory neurons as described above. For example, excitatory and inhibitory neurons in the cortex can be entrained by forming a composite waveform of slow and fast sinusoidal waveforms (e.g., 8 Hz and 140 Hz or 8 Hz and 30 Hz). Excitatory and inhibitory neurons in the hippocampus can be entrained by forming a composite waveform of 4 Hz and 120 Hz. As will become apparent from review of the following disclosure, many more composite waveforms for entrainment of different selected neuronal cell types are provided.

BRIEF DESCRIPTION OF THE SEVERAL VIEWS OF THE DRAWINGS

Some of the drawings submitted herein may be better understood in color. Applicant considers the color versions of the drawings as part of the original submission and reserves the right to present color images of the drawings in later proceedings.

FIGS. 5A-5D. Cell type class identification and characterization of recorded neurons in mice. Sample fluorescent images, electrophysiological firing patterns, cellular morphology, and f-I (frequency-current) plot of neocortical cells used in the recordings. Each recorded cell's f-I curve is plotted, (dark black lines on graphs represent median, error bars: st.d.). Recording internal solution contains a fluorescent dye for localization of patched neuron. (5A) Pyramidal (TI×3+, a Layer 5 specific promoter) (5B) Pvalb, and (5C) SST cells are identified by fluorophore expression in promoter-specific recombinase-dependent transgenic mice.

(5D) After recording, cytosolic material and nucleus can be extracted from the recorded cell to undergo single-cell RNA-sequencing. The transcriptomes of the cells can be mapped to the transcriptomic reference dataset described in Tasic, B. et al. Nature 563, 72-78 (2018) to further confirm cell type. (5D) provides representative rather than actual data.

Figure 6A:
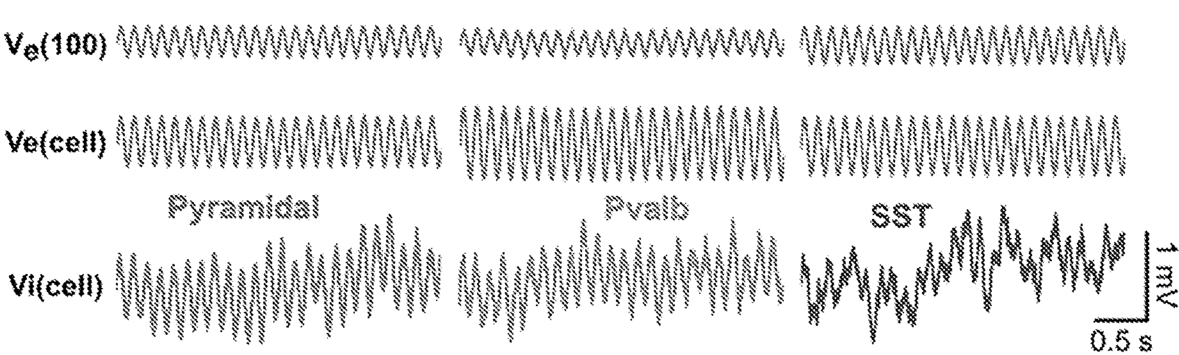
Figure 6B:
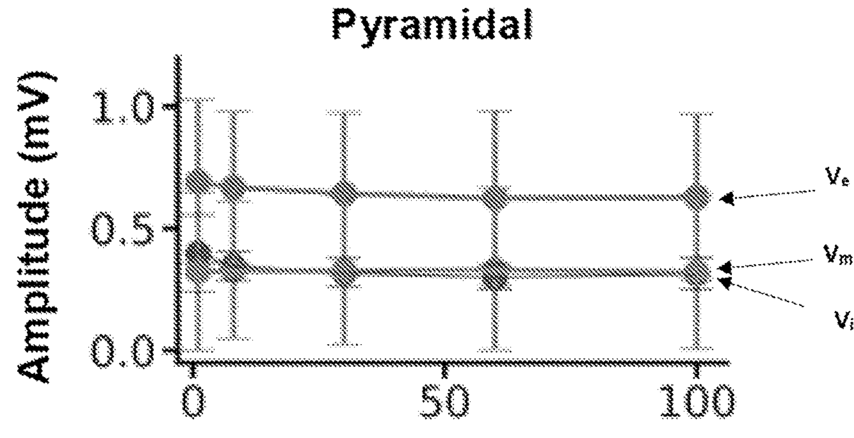
Figure 6B:
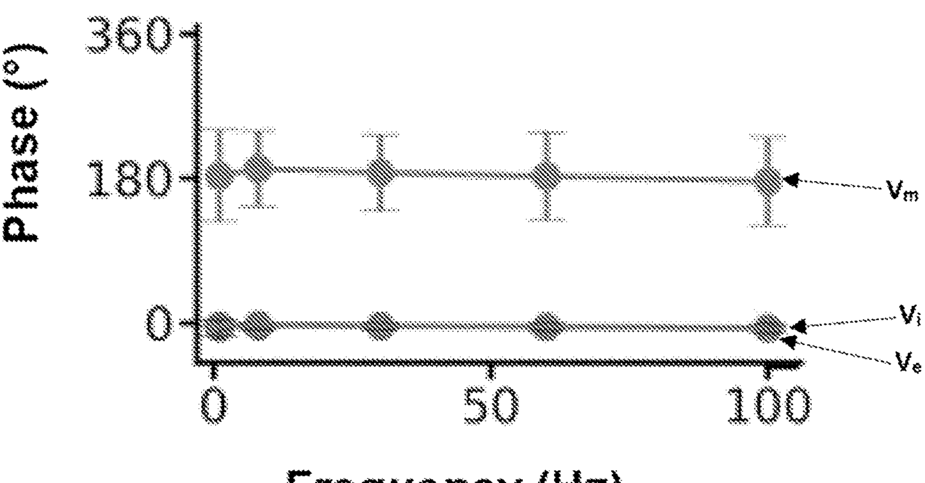
Figure 6B:
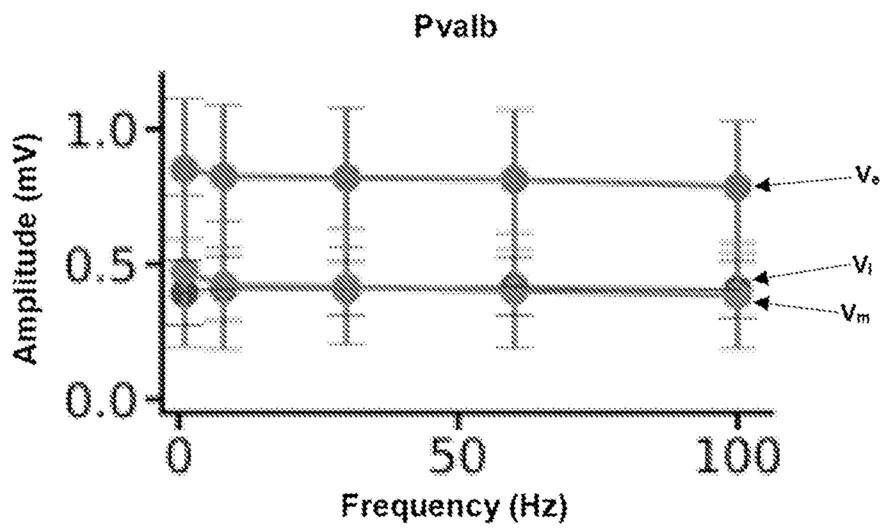
Figure 6B:
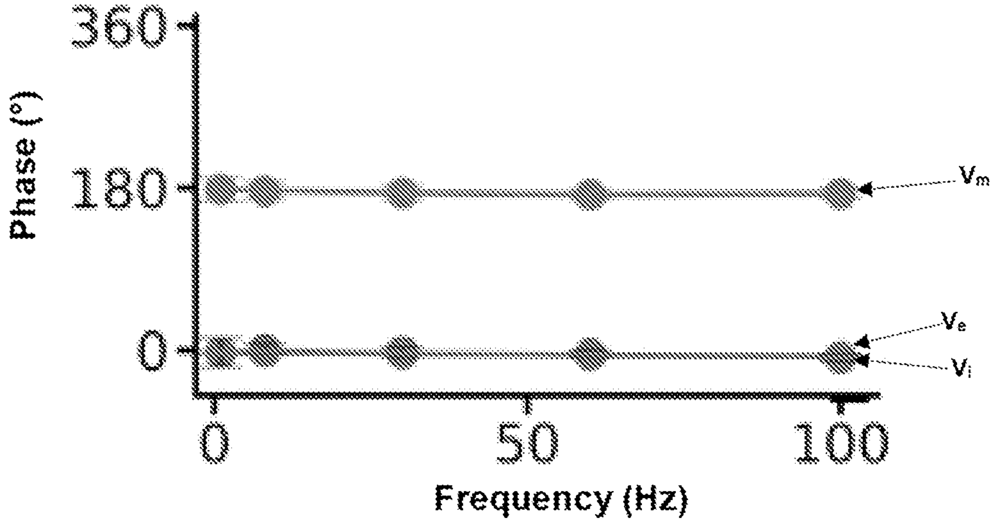
Figure 6B:
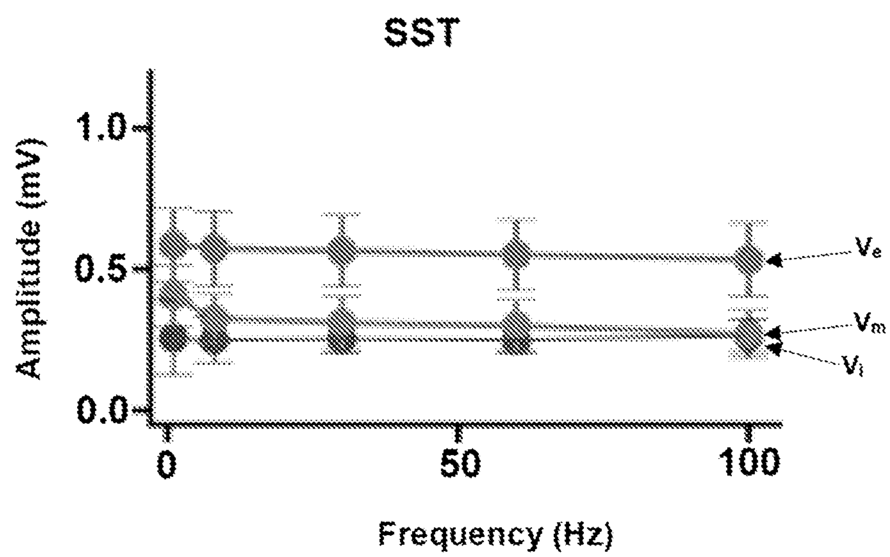
Figure 6B:
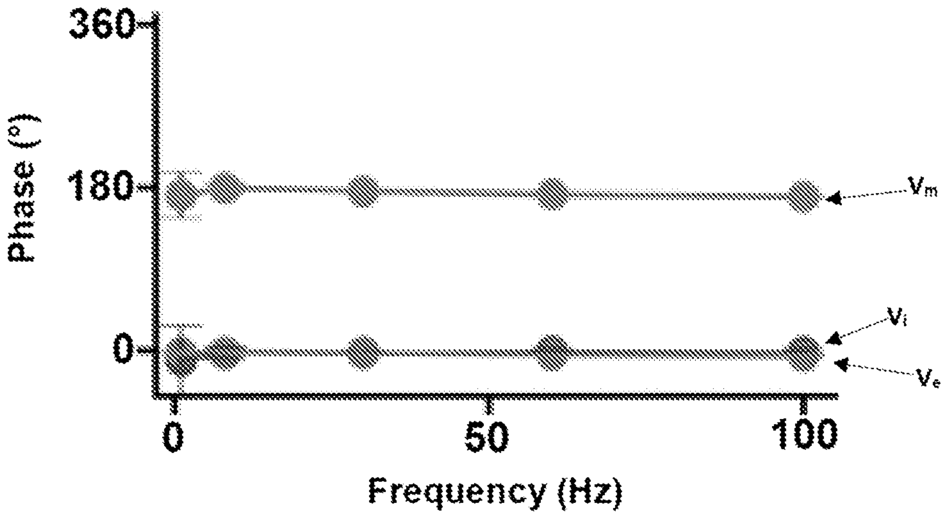

FIGS. 6A, 6B. Subthreshold entrainment to the applied ES in different cell types. (6A) Sample traces showing the entrainment of neuronal Vi to the extracellular ES, for pyramidal, Pvalb, and SST cells. ES was delivered 50 μm from the cell, at 8 Hz and 100 nA. Ve traces measured at different locations (Ve (cell): <15 μm from cell soma, Ve (100): 100 μm from ES). (6B) Average amplitude (top) and phase deflections (bottom) of Ve, Vi, and Vm for each cortical cell type measured in response to ES. (The recorded cells were held at their resting potential while sinusoidal ES was applied at 100 nA from 1 to 100 Hz. n=12 cells (Pyramidal), n=14 cells (Pvalb), n=7 cells (SST). Circles: mean, error bars: st.d.

Figure 7A:
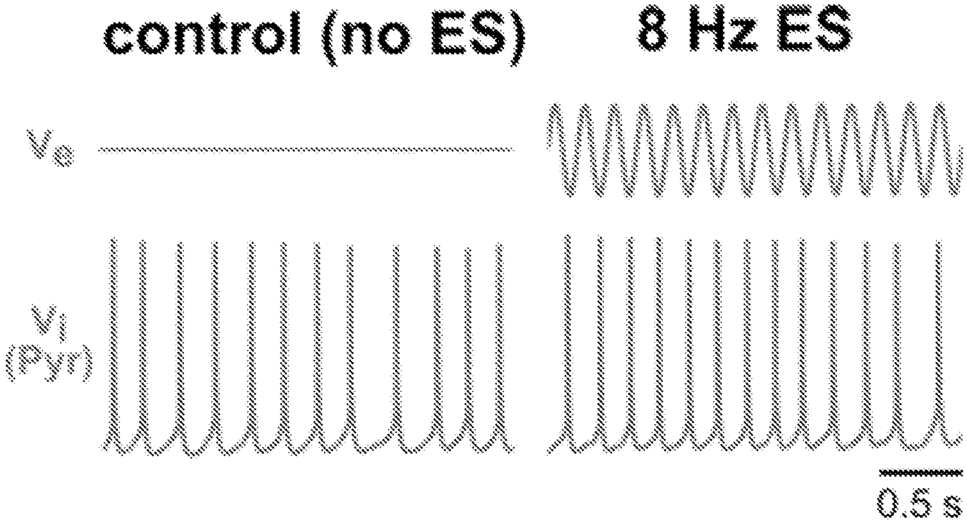
Figure 7B:
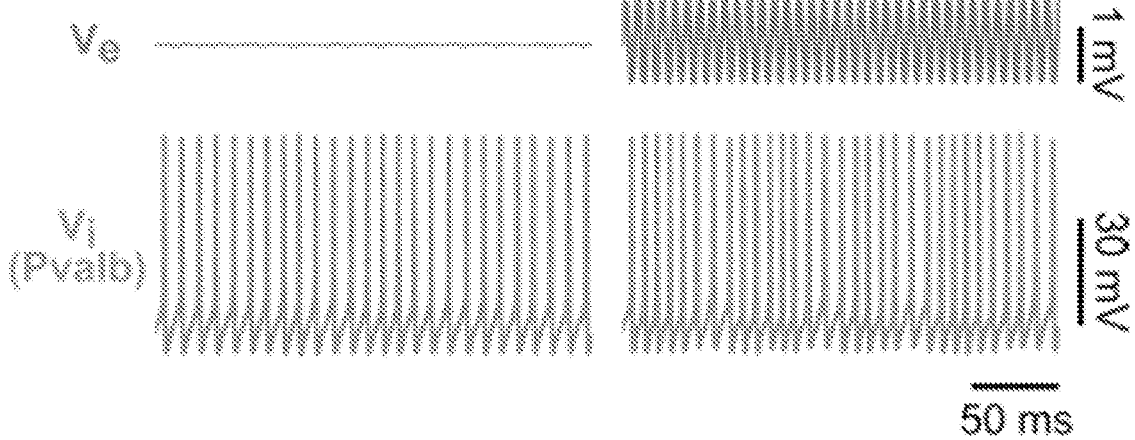

FIGS. 7A, 7B. Application of ES during suprathreshold neuronal activity. Sample traces showing the spiking of (7A) pyramidal and (7B) Pvalb neurons during control situations (when no ES is applied) and during application of ES at 200 nA at various frequencies. Ve is the extracellular voltage measured next to the patched soma (<15 μm distance).

FIGS. 8A-8F. Cell-type-specific entrainment of spiking activity to the extracellular ES. Circular statistics of the spikes for different cell types in (8A, 8B) neocortex and (8C, 8D) hippocampus are analyzed to evaluate the level of spike phase-locking to the extracellular ES. Several ES frequencies and amplitudes were tested, and entrainment was assessed by a decrease in the p-value in Rayleigh's uniformity test and an increase in population vector length. Neocortical and hippocampal cells exhibit strong entrainment to low ES frequencies (8 Hz in neocortex, 4 and 120 Hz in hippocampus), in stark contrast to the Pvalb cells in both regions, demonstrating weak/no entrainment at low frequencies but substantial entrainment at higher frequency. (6E) The −log 10(p-values) of the Rayleigh test are plotted against the ES frequencies tested for pyramidal, SST, and Pvalb cell classes, with the labels (Pyr, SST, Pvalb) at the frequencies showing the highest −log 10(p-value). (6F) For each cell class tested in V1 (top) and CA1 (bottom), the vector length values are shown for control (no ES) conditions and at ES frequencies which best entrain each cell type. Stars indicate significance (p<0.01) of the comparison of spike-phase distribution between control and applied ES conditions (: p<0.01, *: p<0.001, Kuiper's test). (neocortex: (12 cells (Pyr), 15 cells (Pvalb), 5 cells (SST); hippocampus: 12 cells (Pyr), 5 cells (Pvalb)). n: # of spikes per ES frequency/amplitude, p: p-value of Rayleigh's test, lo: amplitude of the applied ES.

FIGS. 9A-9D Cell-type identification and characterization of extracellular ES in human slice tissue and cellular responses. (9A) ES paradigm for human slices set up similarly as in FIGS. 3A, 3B. Recording internal solution also contains a dye for locating the patched neuron located in Layer 5 of the frontal lobe. A pyramidal neuron is identified by the firing pattern (★) and soma morphology visualized post-hoc with biocytin. Pvalb and SST cells are identified by electrophysiological responses to hyperpolarizing and depolarizing current steps injected intracellularly. (9B) The recorded extracellular voltage amplitude is shown at varying distances away from the extracellular stimulation (same as FIG. 4A). ES amplitudes ranged from 25 nA to 200 nA. (9C) Subthreshold and (9D) Spiking entrainment of the human pyramidal neuron as compared to the human fast-spiking neuron, analyzed as in FIGS. 7A-7B. The two cell types show the same cell-type-specific difference in entrainment parameters as seen in the mouse neocortical and hippocampal cell types.

Figure 10A:
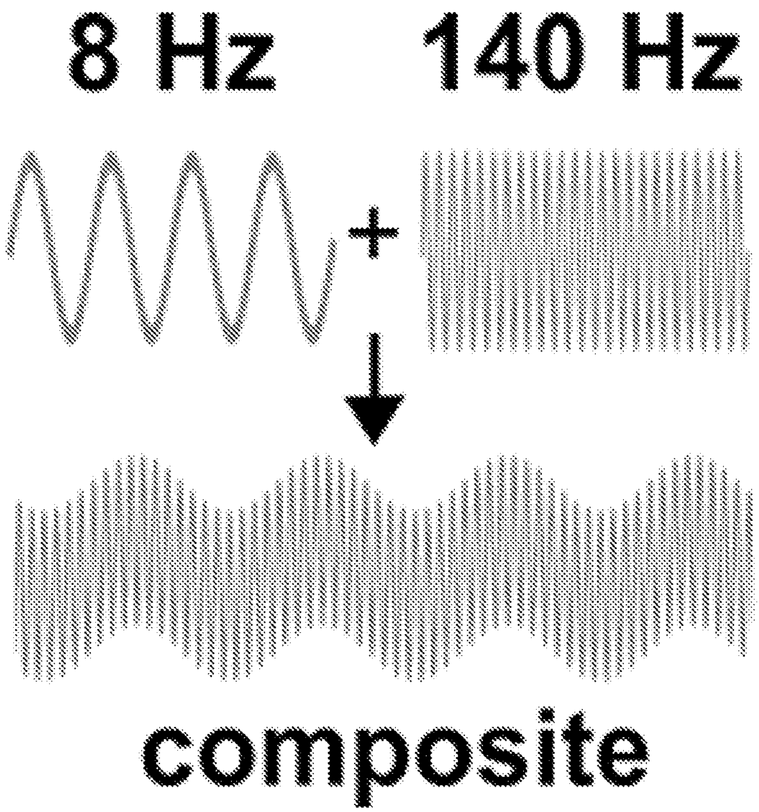
Figure 10C:
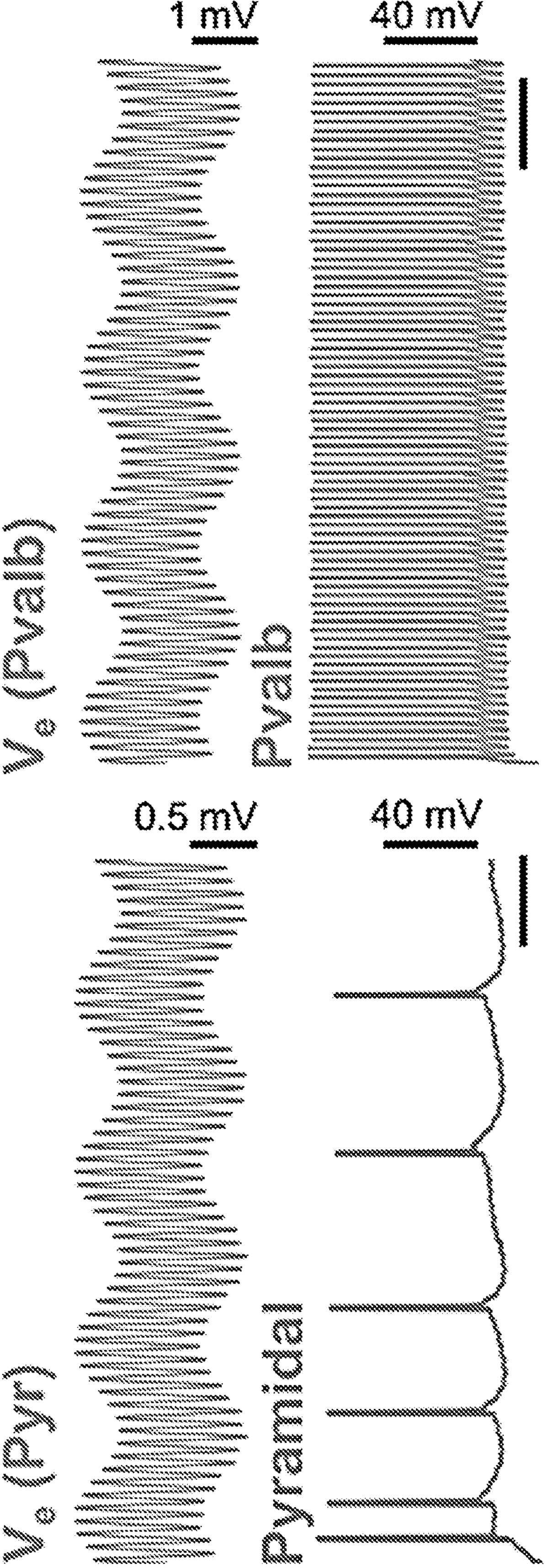

FIGS. 10A-10C. Design and application of composite waveforms for simultaneous control of more than one cell types through ES. (10A) Schematic of ES waveform composition. The composite waveforms were designed to encompass frequencies that entrain the cell types being recorded. (10B) Brightfield (left) and fluorescent (right) image of experimental recording. Two different cell types (pyramidal and Pvalb) were recorded at the same time, with extracellular electrodes placed next to each cell for measuring Ve around the two cells. ES is delivered within 100 μm of both cells. (10C) Sample traces of simultaneous recordings from the pyramidal and Pvalb cells in (10B), with application of a composite ES waveform consisting of 8 Hz (at 25 nA) and 140 Hz (at 150 nA) frequency and amplitude. Ve (Pyr) and Ve (Pvalb) are the extracellular voltage traces recorded next to each cell.

DETAILED DESCRIPTION

The application of extracellular electrical stimulation (ES) to the brain has been widely used to perturb dynamics of brain activity and for therapeutic interventions in neurological disorders such as epilepsy and Parkinson's disease.

Many neurological diseases such as epilepsy, schizophrenia, and autism, are not a disorder of just one cell type class but rather arise from temporal imbalances due to changes to neuronal E/I (excitation/inhibition) balance, caused by changing firing patterns of different cell type classes within the local circuit. The same applies for high-level functioning such as memory formation involving the temporal coordination of distinct circuits and cell types within slower time-scales such as theta or gamma.

Currently, many ES protocols are applied to the brain without consideration for the remarkable diversity of cell types comprising neural circuits. The ability to more precisely control the effects of ES would provide a significant advance.

The current disclosure provides cell-type-specific protocols for the ES entrainment of particular cell types. Entrainment refers to the temporal patterning of subthreshold and spiking dynamics. A neuron becomes entrained by the delivered ES when the temporal patterning of subthreshold and spiking dynamics of a neuron changes to more closely follow the frequency of the delivered ES such that the spiking pattern becomes more predictable. Entrainment includes the "following" of period and/or phase changes to delivered ES for a period of time. In particular embodiments, entrainment is verified by identification of an increased inhomogeneous spike phase distribution (measured in the decreasing p-values of the Rayleigh test) and increased population vector length as the spikes become increasingly entrained to specific Ve-phases.

The current disclosure demonstrates that relatively weak, subthreshold ES amplitudes strongly modulate neuronal spike-timing entrainment in a cell-type-specific manner. The ES-regime with a lower stimulation amplitude, affects the membrane voltage but does not cause measurable changes in spike frequency compared to control conditions. The results disclosed herein led to a number of realizations: (i) when neurons are at subthreshold potentials (i.e. no spiking), cellular entrainment is very similar across cell types and brain areas; (ii) however, different cell types display differential entrainment of their spike-timing patterns to the ES, with the key entrainment parameter being ES frequency. These findings demonstrate cell-type-specific ES entrainment.

In particular embodiments, the current disclosure provides targeted ES entrainment of excitatory versus inhibitory neurons. For example, the current disclosure provides methods of selectively entraining excitatory neurons to ES frequencies below 30 Hertz (Hz) and in particular embodiments to frequencies below 15 Hz, such as 8 Hz and 4 Hz. The current disclosure also provides methods of selectively entraining inhibitory neurons to ES frequencies of at least 30 Hz and depending on the type of inhibitory neuron, to frequencies of 30-60 Hz or to frequencies greater than 100 Hz. As used herein, frequencies are fundamental frequencies unless the context clearly indicates otherwise.

In particular embodiments, the entrained neurons are within the cortex or the hippocampus. In more particular embodiments, the entrained neurons are within the visual cortex (e.g., the primary visual cortex) or the CA1 region of the hippocampus.

Particular embodiments include entraining excitatory cortical or hippocampal neurons with a sinusoidal waveform having a frequency that is below 30 Hz. Particular embodiments include entraining pyramidal neurons within the cortex with a sinusoidal waveform having a frequency of 4-12 Hz. Particular embodiments include entraining pyramidal neurons within the hippocampus with a sinusoidal waveform having a frequency of 4 Hz.

Particular embodiments include entraining inhibitory cortical or hippocampal neurons with a sinusoidal waveform having a frequency that is 30 Hz or greater. Particular embodiments include entraining parvalbumin (Pvalb) neurons within the cortex or hippocampus with a sinusoidal waveform having a frequency that is greater than 100 Hz (e.g., 120 Hz or 140 Hz). Particular embodiments include entraining somatostatin (SST) neurons within the cortex or hippocampus with a sinusoidal waveform having a frequency that is 30 Hz-60 Hz.

Composite waveforms can be generated to entrain an excitatory or inhibitory neuron as described above with another selected cell type. Composite waveforms can also be generated to entrain a combination of excitatory or inhibitory neurons as described above. Particular embodiments include composite waveforms to entrain different types of inhibitory neurons (e.g., Pvalb and Sst).

Aspects of the current disclosure are now described in additional detail as follows: (i) Application and Characteristics of Waveforms; (ii) Methods to Direct Waveforms to Targeted Brain Sites; (iii) ES Delivery Systems; (iv) Experimental Examples; and (v) Closing Paragraphs.

(i) Application and Characteristics of Waveforms. Composite patterns of waveforms can be applied as ES using many different methods. In some cases, the ES is applied by direct conduction. For example, the ES can be performed with an electrode positioned at a target site. The electrode can be implanted permanently, chronically or temporarily. In other cases, the ES is applied externally or without direct contact with the target site structure. For example, the ES can be performed using a probe that transmits ultrasound or electromagnetic energy (e.g., RF) that is captured by the target site.

ES can be delivered according to one or more ES programs that define ES parameter values. Parameter values include, for example, the frequency and/or amplitude of a waveform, the length of time that the ES is delivered (i.e., the period), the time between ES delivery periods, the number of ES delivery cycles, the type of waveform (e.g., single or composite), and selected electrode combinations, positions, and polarities. Per the Fourier theorem, an infinite number of frequencies can be superimposed within a composite waveform. For application to neural cell types, the number of frequencies is only limited by the number of targeted cell types.

Frequencies utilized within the current disclosure include those that are less than 30 Hz (i.e., 1, 2, 3, 4, 5, 6, 7, 8, 9, 10, 11, 12, 13, 14, 15, 16, 17, 18, 19, 20, 21, 22, 23, 24, 25, 26, 27, 28 or 29 Hz) or that are 30 or greater (e.g., 30-1000 Hz) or that are 100 Hz or greater. Particularly useful frequencies in the less than 30 Hz range include 4 Hz and 8 Hz. Particularly useful frequencies in the 30 or greater range include 30 Hz, 50 Hz, 100 Hz, 120 Hz, and 140 Hz. Particularly useful frequencies in the 100 or greater range include 100 Hz, 120 Hz, and 140 Hz. Frequency ranges also include 0-12 Hz; 30-60 Hz; and 100 Hz-160 Hz.

Waveform amplitudes are generally selected to be 500 nanoamperes or less (nA; e.g., 25 nA; 50 nA; 75 nA; 100 nA; 125 nA; 150 nA; 175 nA; 200 nA; 225 nA; 250 nA; 275 nA; 300 nA; 325 nA; 350 nA; 375 nA; 400 nA; 425 nA; 450 nA; 475 nA; or 500 nA) or 500 microamperes or less (μA; e.g., 25 μA; 50 μA; 75 μA; 100 μA; 125 μA; 150 μA; 175 μA; 200 μA; 225 μA; 250 μA; 275 μA; 300 μA; 325 μA; 350 μA; 375 μA; 400 μA; 425 μA; 450 μA; 475 μA; or 500 μA. In general, nA values are used for in vitro entrainment and μA values are used for in vivo entrainment.

Particularly useful frequency/nA combinations include 4 Hz at 50, 100, or 200 nA; 8 Hz at 50, 100, or 200 nA; 30 Hz 50, 100, or 200 nA; 40 Hz 50, 100, or 200 nA; 50 Hz 50, 100, or 200 nA; 60 Hz 50, 100, or 200 nA; 100 Hz 50, 100, or 200 nA; 120 Hz 50, 100, or 200 nA; and 140 Hz 50, 100, or 200 nA. Particularly useful frequency/μA combinations include 4 Hz at 50, 100, or 200 μA; 8 Hz at 50, 100, or 200 μA; 30 Hz 50, 100, or 200 μA; 40 Hz 50, 100, or 200 μA; 50 Hz 50, 100, or 200 μA; 60 Hz 50, 100, or 200 μA; 100 Hz 50, 100, or 200 μA; 120 Hz 50, 100, or 200 μA; and 140 Hz 50, 100, or 200 μA.

For in vivo human uses, applied currents are below regulated levels, for example below the maximum density of current permitted by the United States Food & Drug Administration (FDA).

The time that ES is directed to a targeted region(s) of a subject's brain is dependent on the entrainment purpose. For example, ES can be applied permanently or when a condition is present or predicted to occur. ES can be applied when a subject is performing a task and/or for a period of time after the task is completed (e.g., for 24 hours or 12 hours after the task is completed). ES can be applied for time periods such as 48 hours, 24 hours, 12 hours, or 1 hour. Additional exemplary time periods include between 1 minute and permanently, between 30 seconds and 1 year, between 1 minute and 3 months, between 30 seconds and 48 hours, etc.

When delivery of ES is not permanent, the elapsed time between ES delivery periods is dependent on the entrainment purpose. This elapsed time can be based on when a subject performs a task or when a condition is present or predicted to occur. Exemplary elapsed times between ES delivery periods include 30 minutes, 1 hour, 3, hours, 12 hours, 24 hours, 48 hours, weekly, monthly, yearly, etc.

As indicated previously, the disclosed sinusoidal waveforms can be extrapolated to arbitrarily complex ES waveforms per the Fourier theorem. Per this theorem, any stationary signal can be broken into a series of sinusoidal component functions whose frequencies are those of the fundamental and its harmonics, each component having its proper amplitude and phase.

In particular embodiments, the composite waveforms include at least two different waveforms, i.e., a first waveform that has at least one parameter (e.g., frequency, duration, amplitude, phase symmetry, duty cycle) that is different from a corresponding parameter of a second waveform. The second waveform can be periodically superimposed on the first waveform. The first and/or second waveform can be modified to have a different pattern, intensity, amplitude, frequency, or duration.

In another example, the second waveform is characterized by at least one parameter (e.g., frequency, duration, amplitude, phase symmetry, duty cycle) that is greater or less than the corresponding parameter of the first waveform. For example, the second waveform can have a frequency and/or duration that is/are greater or less than the frequency and/or duration of the first waveform. It will be appreciated that the second waveform can have a frequency of 1 Hz to 1000 Hz, and a duration of 1 ms to 1000 seconds. As noted above, the second waveform is periodically superimposed on the first waveform. For example, the second waveform can be periodically superimposed on the first waveform at a regular interval or, alternatively, at an irregular interval. In another example, the first and/or second waveform can be modified by copying, cutting, pasting, deleting, cropping, appending, or inserting desired segments of waveforms.

It will be appreciated that the composite patterns of stimulation or waveforms can include two, three, four or even more waveforms overlaid on the first waveform, for example up to 1,000. Particular embodiments include generating a composite sinusoidal signal with three relatively low frequency components that are created using an inverse Fourier Transform.

As examples, excitatory and inhibitory neurons in the cortex can be entrained by forming a composite waveform of slow and fast sinusoidal waveforms (e.g., 8 Hz and 140 Hz or 8 Hz and 30 Hz). Excitatory and inhibitory neurons in the hippocampus can be entrained by forming a composite waveform of 4 Hz and 120 Hz. As will become apparent from review of the following disclosure, many more combinations are provided. Particular examples include composite waveforms having a frequency that includes from 0-12 Hz and 30-60 Hz; from 0-12 Hz and 100 Hz-160 Hz; or from 30-60 Hz and 100 Hz-160 Hz. Additional examples include composite waveforms having a frequency that is less than 30 Hz (i.e., 1, 2, 3, 4, 5, 6, 7, 8, 9, 10, 11, 12, 13, 14, 15, 16, 17, 18, 19, 20, 21, 22, 23, 24, 25, 26, 27, 28 or 29 Hz) and a frequency that is 30 or greater. Additional examples include a composite waveform having a frequency that includes from 0-12 Hz with 30 Hz; from 0-12 Hz with 50 Hz; from 0-12 Hz with 60 Hz; from 0-12 Hz with 100 Hz; from 0-12 Hz with 120 Hz; or from 0-12 Hz with 140 Hz. Additional examples include a composite waveform having a frequency that includes from 30-60 Hz with 4 Hz; from 30-60 Hz with 8 Hz; from 30-60 Hz with 100 Hz; from 30-60 Hz with 120 Hz; or from 30-60 Hz with 140 Hz. Additional examples include a composite waveform having a frequency that includes from 100 Hz-160 Hz with 4 Hz; from 100 Hz-160 Hz with 8 Hz; from 100 Hz-160 Hz with 30 Hz; from 100 Hz-160 Hz with 50 Hz; or from 100 Hz-160 Hz with 60 Hz. Additional examples include a composite waveform having a frequency that includes 4 Hz with 8 Hz; 4 Hz with a frequency that is 30 or greater; 4 Hz with 30 Hz; 4 Hz with 50 Hz; 4 Hz with 60 Hz; 4 Hz with 100 Hz; 4 Hz with 120 Hz; or 4 Hz with 140 Hz. Additional examples include a composite waveform having a frequency that includes 8 Hz with a frequency that is 30 or greater; 8 Hz with 30 Hz; 8 Hz with 50 Hz; 8 Hz with 60 Hz; 8 Hz with 100 Hz; 8 Hz with 120 Hz; or 8 Hz with 140 Hz. Additional examples include a composite waveform having a frequency that includes 30 Hz with 50 Hz; 30 Hz with 60 Hz; 30 Hz with 100 Hz; 30 Hz with 120 Hz; or 30 Hz with 140 Hz. Additional examples include a composite waveform having a frequency that includes 50 Hz with 60 Hz; 50 Hz with 100 Hz; 50 Hz with 120 Hz; 50 Hz with 140 Hz; 60 Hz with 100 Hz; 60 Hz with 120 Hz; 60 Hz with 140 Hz; 100 Hz with 120 Hz; 100 Hz with 140 Hz; or 120 Hz with 140 Hz.

(ii) Methods to Direct Waveforms to Targeted Brain Sites. US20170216594 describes methods to deliver selected ES to targeted brain sites using a combination of (1) achieving a selected envelope amplitude at the targeted brain site; (2) isolating currents by making at least one current channel anti-phasic; (3) utilizing different spatial arrays of stimulating electrodes; and/or (4) using current sources to drive interferential currents, rather than voltage sources.

Regarding the envelope amplitude, in application of the ES, two current channels can each produce one original waveform, A and B respectively. The amplitude of waveform A is $E_{ch1}$ and the amplitude of waveform B is $E_{ch2}$. The AM index is the ratio of these two amplitudes: AM index=$E_{ch1}/E_{ch2}$. Interference of the two original waveforms A and B produces an amplitude-modulated (AM) waveform C. The AM waveform C has an envelope. The top of the envelope is a signal, and the peak amplitude of that signal is the envelope amplitude $E_{AM}$. In other words, the "envelope amplitude" of an amplitude-modulated waveform is equal to the peak amplitude of a signal, which signal is the top of the envelope of the amplitude-modulated waveform.

Isolating currents by making at least one of the current channels anti-phasic dramatically reduces current leakage. Reductions in current leakage allow more precise positioning of the selected envelope amplitude at the targeted brain site. In this anti-phasic case, a current source drives two different electric waveforms through balanced pairs of electrodes, one waveform through a first pair of electrodes and a second waveform through a second pair of electrodes. At least one electrode pair is anti-phasic, that is, the phase at the first electrode of the pair is substantially anti-phasic (substantially 180 degrees out-of-phase) from the phase at the second electrode of the pair. When a first signal is "phase-difference-locked" with a second signal, this means that the difference between the phase of the first signal and the phase of the second signal is constant. When a first signal is "phase-locked" with a second signal, this means that a common parameter between the parameter of the first signal and the parameter of the second signal is constant.

In some cases, only one of the electrode pairs is anti-phasic. In other cases, both of the two electrode pairs are anti-phasic. In some cases, a ground or reference electrode is provided to carry any imbalance currents from the paired currents sources and to prevent charge up of the body relative to earth ground. The vast majority (>99%) of the stimulation current created by each electrode pair does not flow through this ground or reference electrode since the current is driven differentially or out of phase with each other. A benefit of this approach is that most of the current is not going through the common ground electrodes. This allows multiple current waveforms to flow independently inside the tissue, eliminating (or greatly reducing) crosstalk between the channels. This permits triangulation of the currents through the conductive medium away from the path of current to the ground.

Particular embodiments include creating first and second electric fields that are temporarily asymmetric. "Temporally asymmetric" means that: (a) the first electric field is a periodic waveform that has a first rise time and a first fall time; (b) the second electric field is a periodic waveform that has a second rise time and a second fall time; and (c) either: (i) the first rise time is longer than the first fall time and the second rise time is shorter than the second fall time, or (ii) the first rise time is shorter than the first fall time and the second rise time is longer than the second fall time.

In particular embodiments, stimulating electrodes are positioned in a wide variety of spatial configurations, including positions in which the electrodes are not in rectangular (or square) configuration. For example, in some embodiments: (a) stimulating electrodes are positioned in a semicircle, or circle, or line; or (b) stimulating electrodes are positioned such that the distance between electrodes of one electrode pair (current channel) is different than the distance between electrodes of the other electrode pair (current channel) or is different than the distance between the two electrode pairs; or (c) the stimulating electrodes are positioned side-by-side, rather than in a crisscross pattern. This feature demonstrates that the positioning of electrodes is adaptable to the structure being stimulated and may be selected so as to control the spatial position of regions in which the envelope amplitude is above a given threshold.

In particular embodiments, current sources are used to drive interferential currents. This, in turn, facilitates precise interferential targeting, because the spatial position of a region with a given envelope amplitude depends in part on the magnitude of the currents in the two interferential current channels.

In certain examples, excitatory neurons are glutamatergic. Glutamatergic neurons express the glutamate transmitters Slc17a6 and/or Slc17a7. They all express Snap25 and lack expression of Gad1/Gad2.

In certain examples, inhibitory neurons are GABAergic. GABAergic neurons express the GABA synthesis genes Gad1/GAD1 and Gad2/GAD2. Sst and Pvalb GABAergic neurons are developmentally derived from neuronal progenitors in the medial ganglionic eminence (MGE).

Sst GABAergic neurons particularly are found in many neocortical layers, but especially frequent in lower layers (L5-L6). They highly express the neurotransmitter somatostatin (Sst), and frequently block dendritic inputs to postsynaptic neurons.

Pvalb GABAergic neurons are found in many neocortical layers, but are especially frequent in lower layers (L5-L6). They highly express the calcium-binding protein parvalbumin (Pvalb), express neuropeptide Tac1, and frequently dampen the output of postsynaptic neurons.

The cortex is the outer layer of the brain (also referred to as the grey matter). The four lobes of the cortex include the frontal lobe, parietal lobe, temporal lobe, and occipital lobe.

The hippocampus is a C-shaped brain structure embedded deep into the temporal lobe. The hippocampus is the posterior part of limbic lobe while the frontal part is amygdala. The hippocampus is anatomically subdivided into subfields known as the CA1-CA4 regions, each populated by a stereotypical cytoarchitecture with predictable synaptic interconnections between subfields (Duvernoy, The Human Hippocampus: Functional Anatomy, Vascularization And Serial Sections With Mn (2005)). The CA1 subfield serves in the main output pathway of the hippocampal formation. The hippocampus is known to play a role in learning, memory and spatial navigation.

(iii) ES Delivery Systems. The present disclosure can be implemented using a variety of different ES delivery systems.

In particular embodiments, an ES delivery system can include an ES generator and one or more leads carrying electrodes. In some cases, electrodes can be coupled to an ES generator via one or more percutaneous leads or fully implanted leads. Alternatively, the ES delivery system can be leadless.

In particular embodiments, electrodes of an ES delivery system can be ring electrodes. Ring electrodes are relatively easy to program and are typically capable of delivering an electric field to any tissue adjacent to their corresponding leads. As indicated above, in other examples, electrodes can have different configurations, such as a complex electrode array geometry capable of producing shaped electric fields. The complex electrode array geometry generally includes multiple electrodes (e.g., partial ring or segmented electrodes) around the perimeter of individual leads. In this manner, ES can be directed in a specific direction to stimulate a smaller volume of tissue.

Leads within ES delivery systems are often in the form of elongated cylinders, however, paddle leads, spherical leads, bendable leads, or any other type of shape effective for administering ES to a subject can be used.

Particular embodiments of ES delivery systems include a processor, an ES generator, a sensing module, memory, a switch module, a telemetry module, a user interface, and a power source.

The processor can control the ES generator to generate and deliver ES via electrodes. The processor can include any one or more of microprocessors, controllers, digital signal processors (DSPs), application specific integrated circuits (ASICs), field-programmable gate arrays (FPGAs), and discrete logic circuitry. The functions attributed to processors described herein can be provided by a hardware device and embodied as software, firmware, hardware, or any combination thereof.

The sensing module senses bioelectrical brain signals of a subject via electrodes. The electrodes can be implanted or can external (e.g., scalp electrodes). The sensing module can include circuitry that measures the electrical activity of a particular region of a subject's brain (e.g., cortex or hippocampus).

In some examples, the sensing module can sense brain signals substantially at the same time that ES is delivered to a subject. In other examples, the sensing module can sense brain signals at a time that is different from the time of ES delivery.

The sensing module can include circuitry for determining a voltage difference between, for example, two electrodes, which generally indicates the electrical activity within the particular region of brain. One of the electrodes can act as a reference electrode.

The output of the sensing module can be received by the processor. In some cases, the processor can apply additional processing to the bioelectrical signals, e.g., convert the output to digital values for processing and/or amplify the bioelectrical brain signal. In addition, in some examples, the sensing module or processor can filter the signal from the selected electrodes in order to remove undesirable artifacts from the signal, such as noise from cardiac interference. The sensing module and processor can communicate via wired or wireless communication techniques.

In some examples, the sensing module can include circuitry to tune to and extract a power level of a particular frequency band of a sensed brain signal. Thus, the power level of a particular frequency band of a sensed brain signal can be extracted prior to digitization of the signal by the processor. By tuning to and extracting the power level of a particular frequency band before the signal is digitized, it can be possible to run frequency domain analysis algorithms at a relatively slower rate compared to systems that do not include a circuit to extract a power level of a particular frequency band of a sensed brain signal prior to digitization of the signal. In some examples, the sensing module can include more than one channel to monitor simultaneous activity in different frequency bands, i.e., to extract the power level of more than one frequency band of a sensed brain signal. These frequency bands can include an alpha frequency band (e.g., 8 Hz to 12 Hz), a beta frequency band (e.g., 12 Hz to 35 Hz), a gamma frequency band (e.g., between 35 Hz to 200 Hz), or other frequency bands.

In some examples, the sensing module can include an architecture that merges chopper-stabilization with heterodyne signal processing to support a low-noise amplifier. Exemplary amplifiers are described in U.S. Patent Publication Nos. 2009/0082691 and 2009/0082691.

Examples of signals that can be monitored by sensing modules include electroencephalogram (EEG) signals, electrocorticogram (ECoG) signals, local field potentials (LFP) sensed from within one or more regions of a subject's brain and/or action potentials from single cells within the subject's brain.

In some examples, the sensing module can be configured to check or otherwise verify that cells have been entrained by the delivered ES.

Memory can include any volatile or non-volatile media, such as a random-access memory (RAM), read only memory (ROM), non-volatile RAM (NVRAM), electrically erasable programmable ROM (EEPROM), flash memory, and the like. Memory can store computer-readable instructions that, when executed by the processor deliver ES and/or sense signals. Memory can be considered, in some examples, a non-transitory computer-readable storage medium including instructions that cause one or more processors to implement one or more of the example techniques described in this disclosure. The term "non-transitory" can indicate that the storage medium is not embodied in a carrier wave or a propagated signal. However, the term "non-transitory" should not be interpreted to mean that memory is non-movable. As one example, memory can be moved between and among devices. In certain examples, a non-transitory storage medium can store data that can, over time, change (e.g., in RAM).

In particular embodiments, the processor controls a switch module to sense bioelectrical brain signals with selected combinations of electrodes. In particular, the switch module can create or cut off electrical connections between the sensing module and selected electrodes in order to selectively sense bioelectrical brain signals, e.g., in particular portions of a subject's brain. The processor can also control the switch module to apply stimulation signals generated by the ES generator to selected combinations of electrodes. In particular embodiments, the switch module can couple stimulation signals to selected conductors within leads, which, in turn, deliver the stimulation signals across selected electrodes. The switch module can be a switch array, switch matrix, multiplexer, or any other type of switching module configured to selectively couple stimulation energy to selected electrodes and to selectively sense bioelectrical brain signals with the selected electrodes. Hence, in these embodiments, the ES generator is coupled to the electrodes via the switch module and conductors within leads. In some examples, however, a switch module is not included. For example, an ES delivery system can include separate current sources and sinks for each individual electrode.

A telemetry module can support wireless communication between an ES delivery system and an external programmer or another computing device under the control of a processor. For example, the processor of an ES delivery system can transmit bioelectrical brain signals, via a telemetry module to a telemetry module within the external programmer or another external device. Telemetry modules can accomplish communication by radiofrequency (RF) communication techniques or via proximal inductive interaction of the ES delivery system with the external programmer. Accordingly, a telemetry module can send information to an external programmer or other device on a continuous basis, at periodic intervals, or upon request.

A user (e.g., clinician, veterinarian, researcher, or subject), can interact with the external programmer through a user interface. The user interface generally includes a display, such as an LCD or LED display or other type of screen, to present information related to ES. The user interface can also include an input mechanism to receive input from the user. The input mechanisms can include, for example, buttons, a keypad (e.g., an alphanumeric keypad), a peripheral pointing device or another input mechanism that allows the user to navigate through user interfaces.

A power source delivers operating power to various components of the ES delivery system. The power source can include a small rechargeable or non-rechargeable battery and a power generation circuit to produce the operating power. Recharging can be accomplished through proximal inductive interaction between an external charger and an inductive charging coil within the ES delivery system. In some examples, power requirements can be small enough to allow the ES delivery system to utilize subject motion and implement a kinetic energy-scavenging device to trickle charge a rechargeable battery. In other examples, traditional batteries can be used.

Figure 1A:
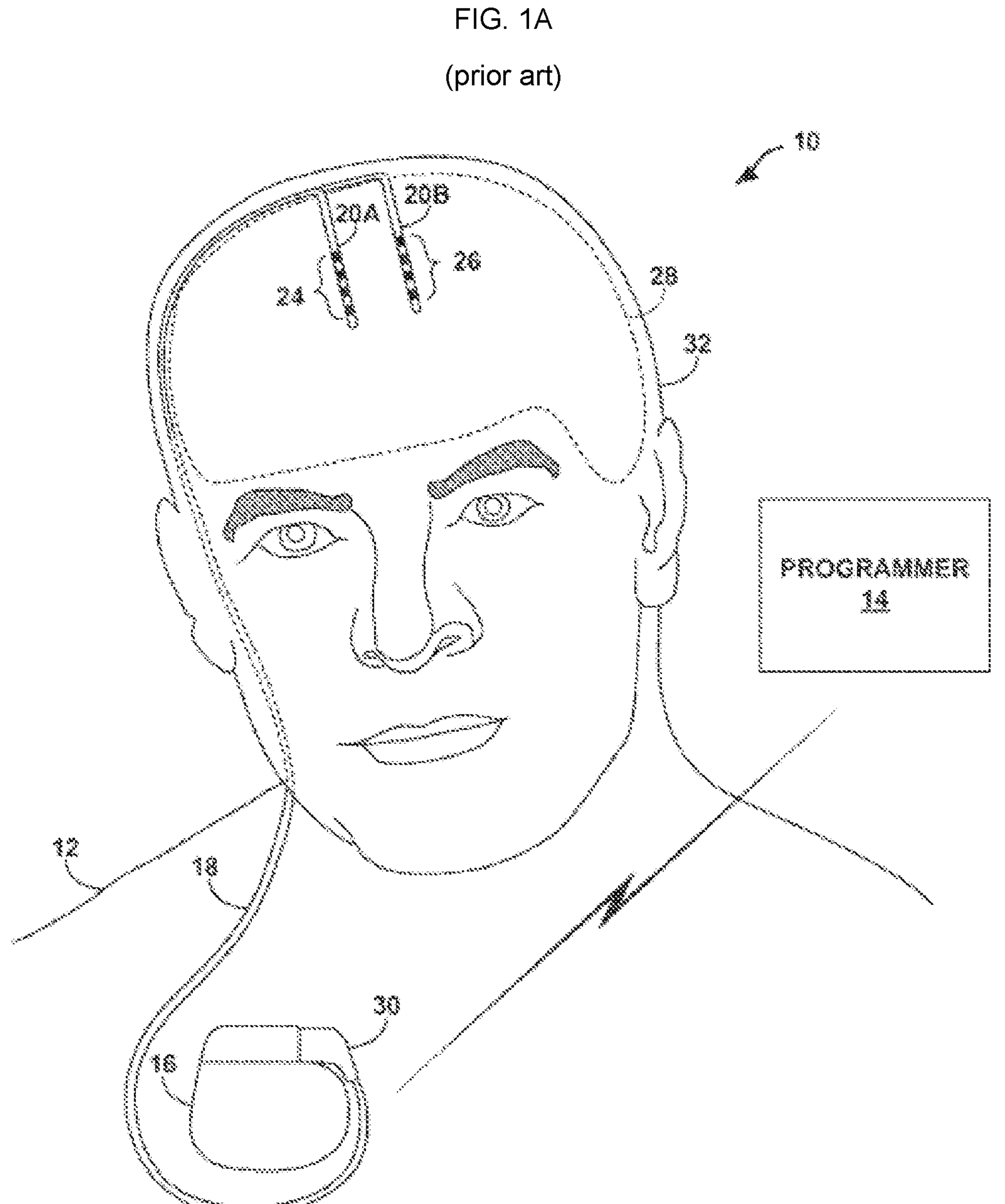
FIGS. 1A-1C. Exemplary ES delivery systems as described in (10A) U.S. Pat. No. 9,878,161; (10B) U.S. Pat. No. 8,880,173; and (10C) JP 2017000835.

FIG. 1A depicts an exemplary ES delivery system 10 as described in U.S. Pat. No. 9,878,161 that includes an implantable device (ID) 16. This ES delivery system 10 also includes device programmer 14, lead extension 18, and one or more leads 20A and 20B (collectively "leads 20") with respective sets of electrodes 24, 26. ID 16 includes a stimulation module that includes an ES generator that generates and delivers ES to one or more regions of brain 28 of subject 12 via a subset of electrodes 24, 26 of leads 20A and 20B, respectively.

In the example shown, ID 16 can be implanted within a subcutaneous pocket above the clavicle of subject 12. Implanted lead extension 18 is coupled to ID 16 via connector block 30 (also referred to as a header), which can include, for example, electrical contacts that electrically couple to respective electrical contacts on lead extension 18. The electrical contacts electrically couple the electrodes 24, 26 carried by leads 20 to ID 16. Lead extension 18 traverses from the implant site of ID 16 within a chest cavity of subject 12, along the neck of subject 12 and through the cranium of subject 12 to access brain 28. Generally, ID 16 is constructed of a biocompatible material that resists corrosion and degradation from bodily fluids. ID 16 can include a hermetic housing 34 to substantially enclose components, such as a processor, ES delivery module, and memory.

The depicted ES delivery system includes an external programmer 14 that wirelessly communicates with ID 16 as needed to provide or retrieve information. Programmer 14 can be a hand-held computing device with a display viewable by a user and an interface for providing input to programmer 14 (i.e., a user input mechanism). In other examples, programmer 14 can be a larger workstation or a separate application within another multi-function device, rather than a dedicated computing device. For example, the multi-function device can be a notebook computer, tablet computer, workstation, cellular phone, personal digital assistant or another computing device that can run an application that enables the computing device to operate as a secure device programmer 14. A wireless adapter coupled to the computing device can enable secure communication between the computing device and ID 16.

Figure 1B:
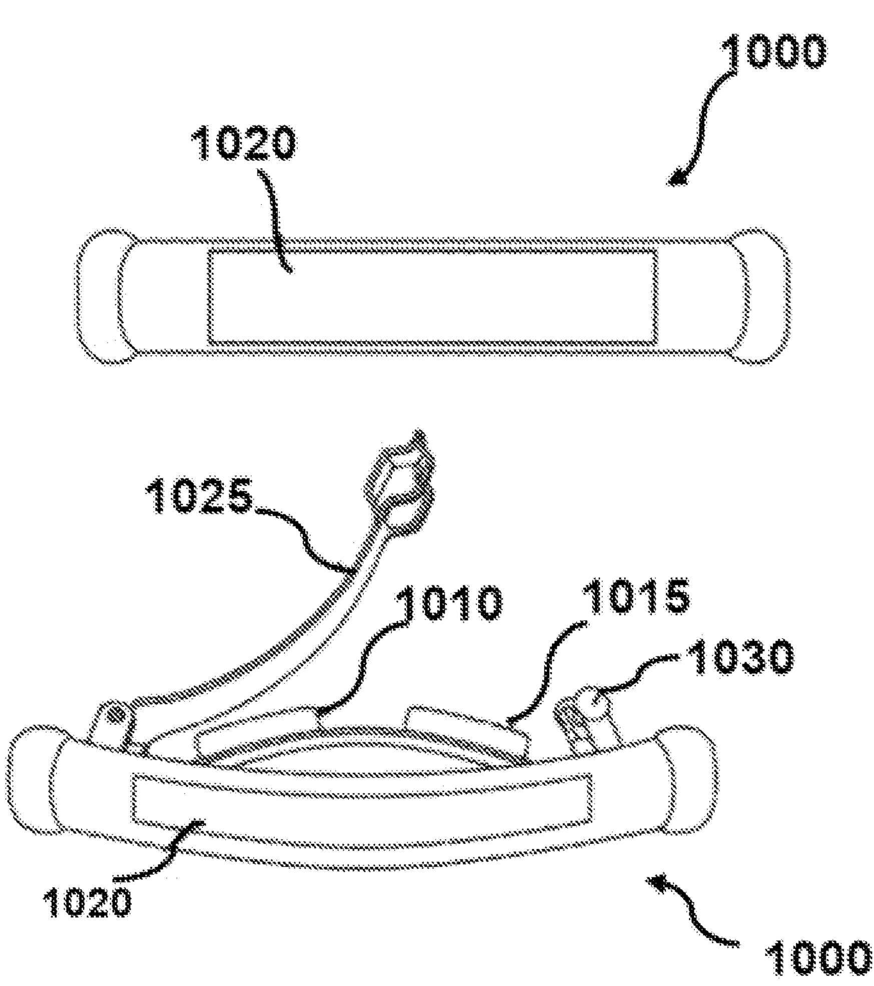

FIG. 1B depicts an example of a non-evasive ES delivery system as described in U.S. Pat. No. 8,880,173. The device includes a barrette 1000 including a printed circuit board and associated electronic circuitry 1020 to generate an electric field in a pair of electrodes (e.g., anode 1010, cathode 1015) disposed proximate the head when worn. A hinged arm 1025 of the barrette 1000 is releasably secured by a locking mechanism 1030.

Figure 1C:
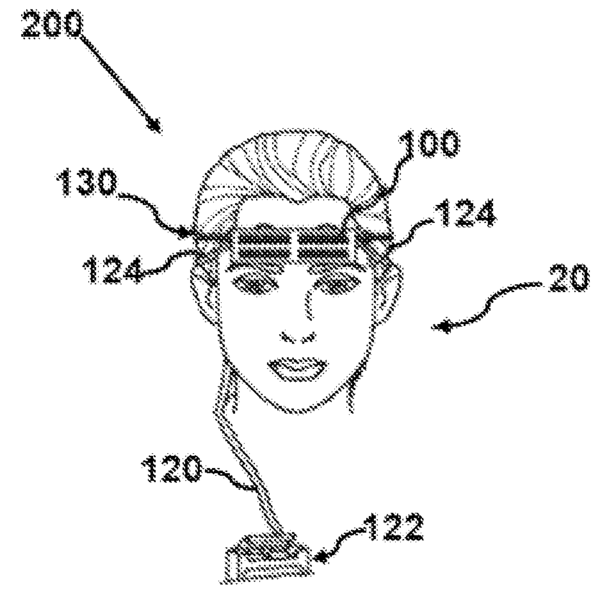
Figure 1C:
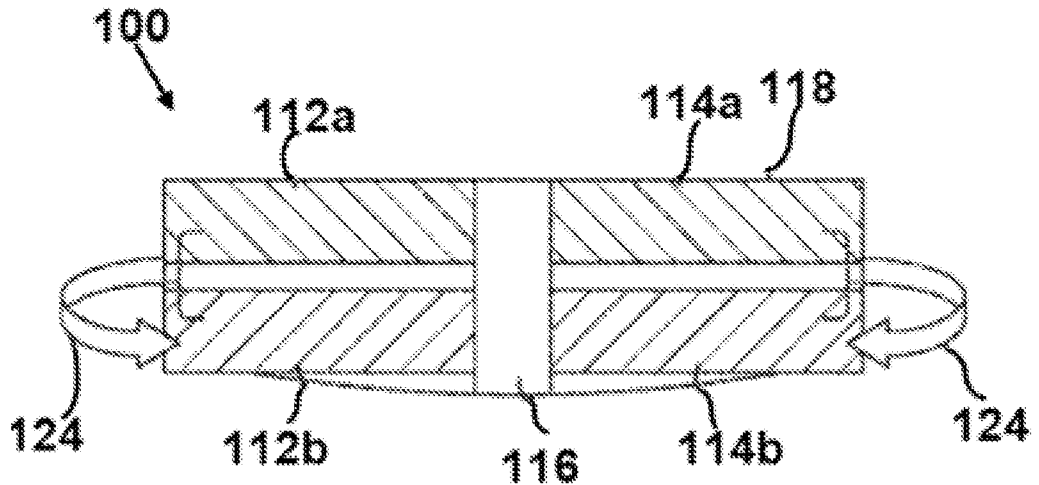
Figure 2A:
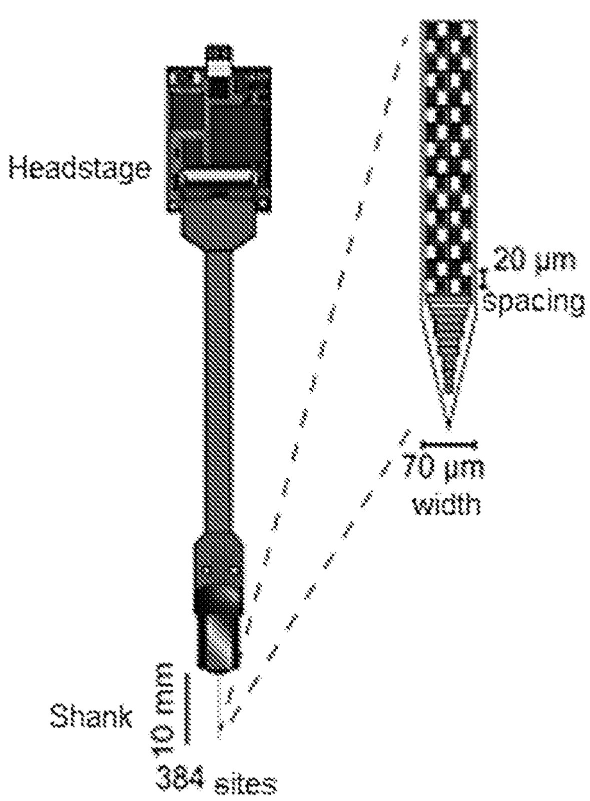
FIGS. 2A-2C. (2A) Diagram of the Neuropixels (NP) probe (Jia, et al., Journal of Neurophysiology 121, 1831-1847 (2019)), consisting of 384 selectable recording sites (dark squares), 20 μm apart. (2B) Three probes and the stimulating electrode mounted on a recording rig, each under the control of a 3-axis manipulator. (2C) Schematic diagram of ES delivery setup in (2B).
Figure 2B:
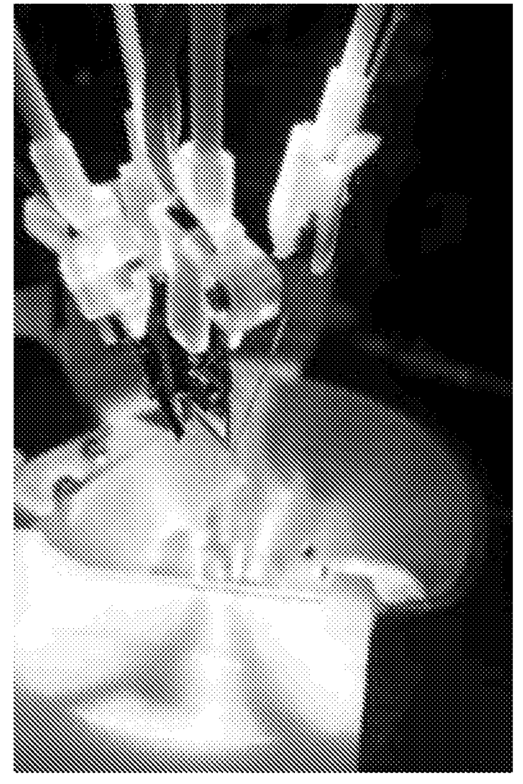
Figure 2C:
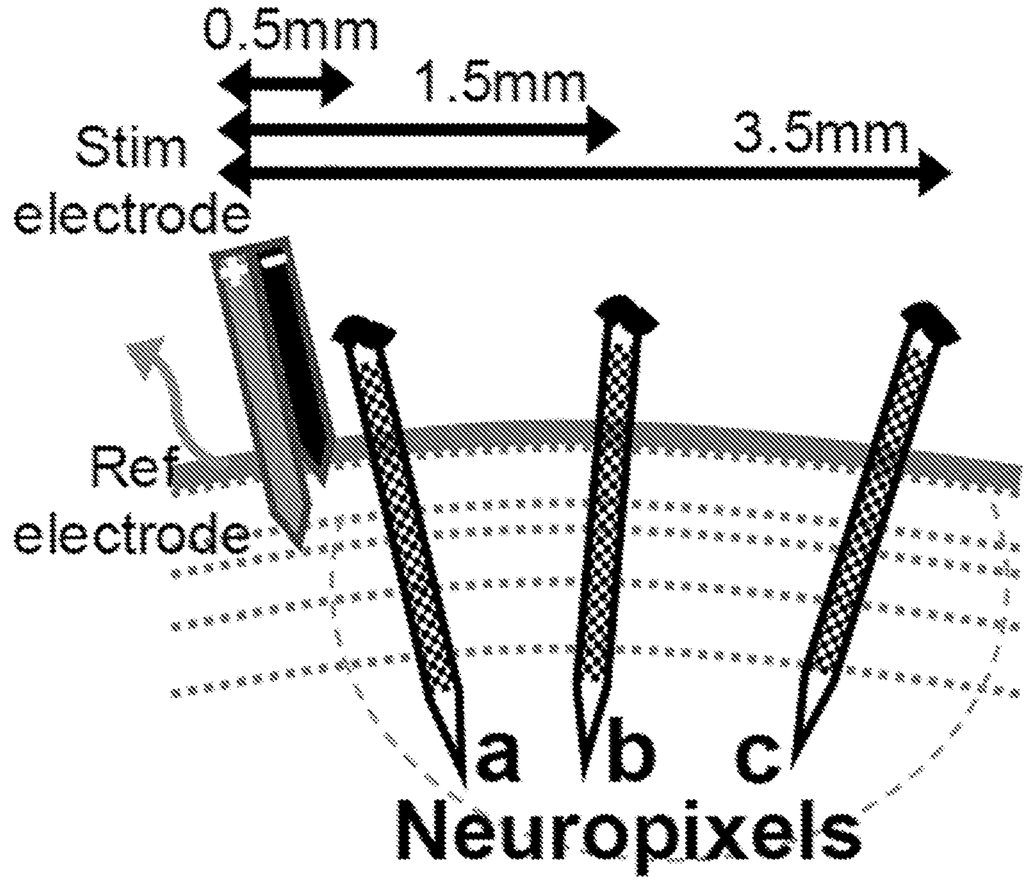

FIG. 1C depicts another example of a non-evasive ES delivery system as described in JP 2017000835A. The depicted ES delivery system 200 includes an electrode assembly 100, an electric cable or wire 120, and an external neurostimulator 122 that can be attached to a subject 20. The electrode assembly 100 can be wirelessly connected to neurostimulator 122 or can be connected by a lead wire 124 connected to an electrical cable 120.

The depicted electrode assembly 100 is a bilateral electrode having a first contact pair 112*a*, 112*b* disposed on a first region of the subject, and a second contact pair 114*a*, 114*b* disposed on a second region of the subject. The first and second contact pairs are connected to each other by an insulating connection region 116. Thus, the electrode assembly 100 includes an inner contact surface 118 that contacts the subject at four contact areas. The inner contact surface 118 includes a buffered gel-like adhesive that provides good conductivity while minimizing skin irritation. The electrode assembly 100 further includes a retaining element 130 configured to secure the electrode assembly to the subject's head (e.g., an elastic band or strap, a hat or cap, or an adhesive).

For more information on non-evasive ES delivery systems see: U.S. Pat. Nos. 4,856,526, 8,554,324B2, US20060173510A1, U.S. Pat. No. 8,948,875B2, and EP2651504B1.

In some instances, the present disclosure can be implemented using an ES delivery system as described in U.S. Pat. No. 8,112,154. This ES delivery system includes a memory that stores waveform data for first and second input waveforms; a playback system that provides first and second output waveforms, based on the first and second input waveforms in the memory, to form a composite pattern of stimulation or waveform, the first output waveform being different than the second output waveform, the second output waveform being periodically superimposed on the first output waveform; a stimulation electrode; and a controller in communication with the stimulation electrode, the controller being configured to control application of the composite pattern of stimulation or waveform to a target site in the brain of a subject.

Particular embodiments can use an electrode for delivering ES and a Neuropixel (NP) probe for recording. The NP probe is a multi-channel recorder described in, for example, Jun, et al., Nature 551, 232— 236 (2017); Siegle, et al., biorxiv.org/lookup/doi/10.1101/805010 (2019); Jia, et al., Journal of Neurophysiology 121, 1831-1847 (2019); Denman & Reid, biorxiv.org/lookup/doi/10.1101/812859 (2019); and Bennett, et al., Neuron 102, 477-492.e5 (2019). The NP probe contains 960 sites on a 10 mm shank and is able to simultaneously record from 384 channels placed 20 μm apart.

Each probe typically records hundreds of extracellular units (Jun, et al., Nature 551, 232-236 (2017)) that can be used to test for ES entrainment under different conditions (e.g. close vs. far from the stimulation location). The NP probes have been used to characterize Ve in response to varying ES frequencies (1, 4, 8, 40 Hz), and the spread of that field for moderate ES-amplitudes leaving the network mostly subthreshold (Histed, et al., Neuron 63, 508-522 (2009)).

Extracellular ES can be applied through a bipolar (150 μm spacing) platinum/iridium electrode on awake, head-fixed mice (for example, running freely on a rotating disk). Concurrent large-scale multi-channel recordings of extracellular action potentials and LFP using the NP probes can be conducted.

Single-channel EAP features that can be investigated include spike width, amplitude, the ratio of the spike peak to trough, and the recovery slope after the peak (Jia, et al., Journal of Neurophysiology 121, 1831-1847 (2019); Mitchell, et al., Neuron 55, 131-141 (2007); Niell & Stryker, J. Neurosci. 28, 7520-7536 (2008)). Multi-channel features incorporate the spread and velocity of the unit waveform detected by multiple close contacts on the probe (Jia, et al., Journal of Neurophysiology 121, 1831-1847 (2019); Wei, et al., In vivo cortical circuit characterization in a large-animal model through massively parallel extracellular Neuropixels recordings. Program No. 252.17. 2019 Neuroscience Meeting Planner. Chicago, IL: Society for Neuroscience, 2019. Online).

Extracellular ES can be applied as sinusoidal waveforms. Three to six NP probes can be placed at distances 0.5 mm to 3.5 mm away from the stimulation site. The effects of ES parameters can be systematically tested and characterized by varying both the amplitude and frequency of the applied ES. ES frequencies encompassing clinical EEG bands (e.g. delta to lower gamma, at 1, 4, 8, 30 Hz), along with the high-frequency stimulation (>100 Hz) used for therapeutic applications such as deep brain stimulation (DBS) can be delivered. These frequencies can be applied with extracellular ES amplitudes ranging from 20 to 200 μA with unit activity monitored both during ES (duration: 10 seconds) as well as before and after ES delivery (control).

A subject within the context of the current disclosure can include a human, veterinary animal (e.g., dog, cat, reptile, bird) livestock (e.g., horse, cow, goat, pig, chicken) or research animal (e.g., monkey, rat, mouse, fish).

In particular embodiments, ES is applied while a subject performs a task, such as a cognitive task, a learning task, a visual task, or a movement-based task and/or after the subject has completed the task. In particular embodiments, ES is applied while a subject engages in an activity, such as meditation, mental rehearsal, sleep, or sport and/or after the subject has completed the activity. In some embodiments, ES is applied while the subject receives a treatment and/or after the subject has completed the treatment.

(iv) Experimental Examples. A combination of state-of-the-art techniques were used that allowed deep characterization of ES effects at the single-cell and circuit-level. At the single-cell level, a multipatch electrophysiology system was used to simultaneously stimulate and record intracellularly from the soma, and from multiple extracellular locations near the soma of identified neurons. Beyond ES-effects on excitatory neurons, important inhibitory cell types, e.g. parvalbumin (Pvalb)- and somatostatin (SST)-expressing types, known to critically impact cortical function were also entrained.

Figure 3A:
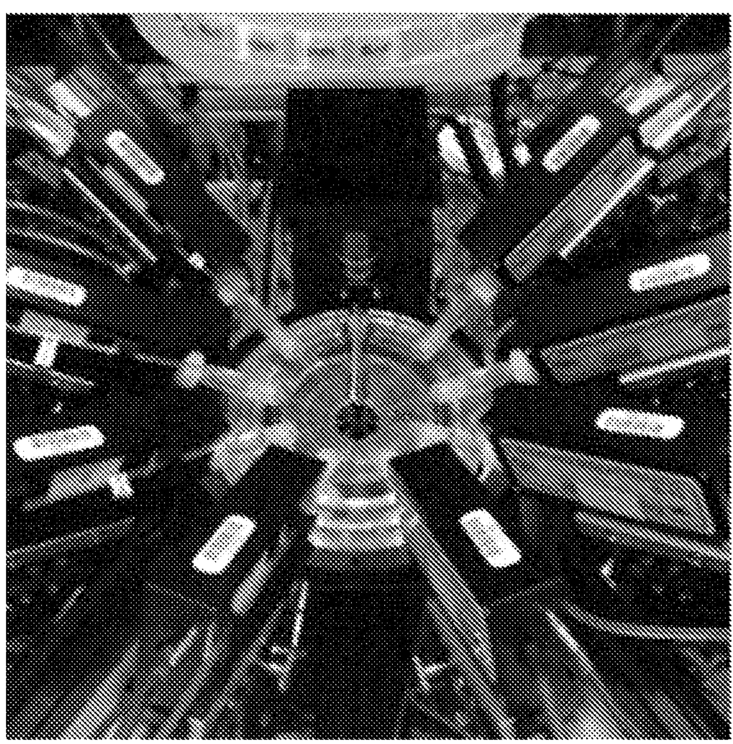
FIGS. 3A, 3B. ES paradigm in vitro. (3A) A customized multipatch electrophysiology rig with 8 electrodes for intracellular and extracellular stimulation, whole-cell recordings, and extracellular recordings from multiple locations near the soma within an experiment. (3B) Sample recording setup in a mouse cortical slice with positioned electrodes. ★ represents an extracellular stimulating electrode; ▲ represents a patched neuron; ● represents an intracellular recording electrode; ■ represent extracellular electrodes recording the extracellular voltage at different locations.
Figure 3B:
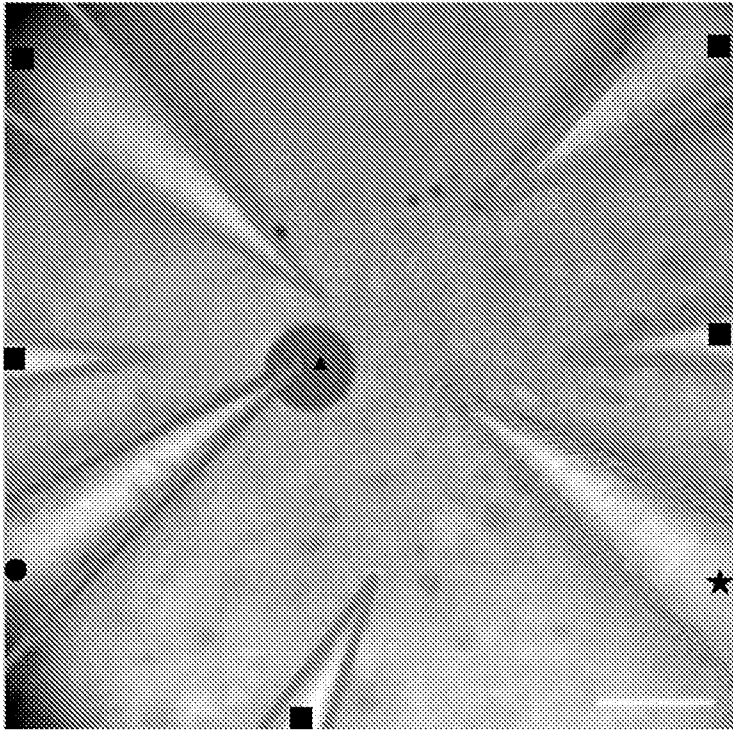
Figure 4A:
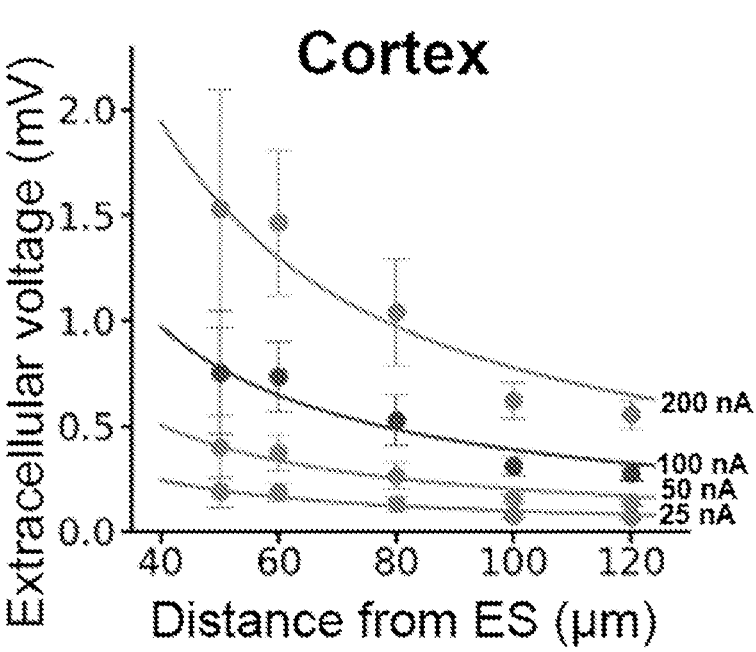
FIGS. 4A, 4B. Spread of the applied extracellular electric field in rodent brain. (4A) Recorded extracellular voltage amplitude (circles: average, error bars: st.d.) with solid lines indicating the best fit (least-squares) of the point-source approximation. (4B) The electric field (calculated as the voltage difference fit across recording sites for a current amplitude) elicited by the extracellular ES. Circles represent extracellular voltage amplitude from each site. ★ represent mean and error bars: st.d. ES amplitude for (4A) and (4B) ranged from 25 to 200 nA. Recordings from mouse cortex V1 Layer 5, n=33 sites.
Figure 4B:
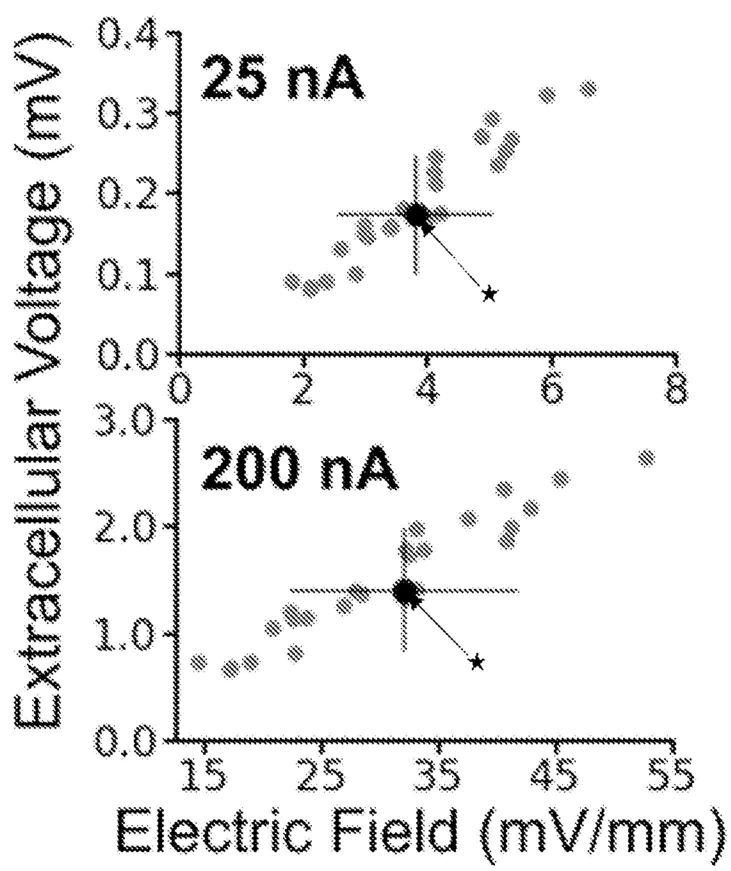

The in vitro extracellular ES framework analyzes the effects of the electric fields generated by extracellular ES, on different cell type classes. A customized 8-pipette multipatch electrophysiology rig was used to enable both intracellular and extracellular stimulation, whole-cell recordings, and extracellular recordings from multiple sites near the soma. Neurons were patch-clamped at their soma while sinusoidal ES of varying amplitude and frequency were simultaneously delivered via an electrode positioned 50 μm away from the soma (FIGS. 3A, 3B). In addition to the cellular responses, the spread of the electric field near the stimulation area was also characterized with extracellular electrodes placed near the cell soma (50-120 μm; FIGS. 4A, 4B).

Electrode distance and placement were measured with software connected to the microscope and micromanipulators for accurate tracking of the hardware and cell position. Recordings were saved in the open source nwb (Neurodata Without Borders) format to facilitate public data archival. Teeters, et al., Neuron 88, 629-634 (2015).

In rodent, recordations were taken from cortical (neocortical primary visual cortex (V1) and hippocampal CA1) regions, in 350 μm-thick acute slices prepared from adult (P40-55) mice (both from male and female mice). In human, human acute brain slices were prepared from tissue obtained from patients undergoing surgery for epilepsy or tumor resection in the temporal or frontal lobe. (The tissue obtained is situated away from the core pathological site and determined not to be of diagnostic value). Mouse and human tissue were prepared with standardized slice preparation reagents and protocols as described in Kalmbach, et al., Neuron 100, 1194-1208.e5 (2018); Hodge, et al., Nat Commun 11, 1172 (2020); Gouwens, biorxiv.org/lookup/doi/10.1101/2020.02.03.932244 (2020); and Seeman, et al., eLife 7, e37349 (2018).

Figure 5B:
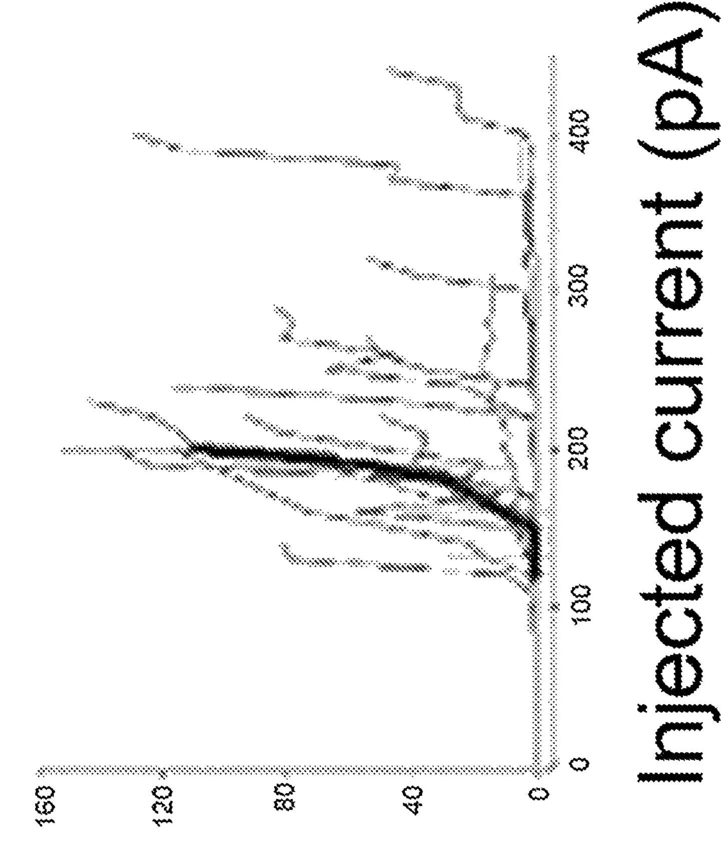
Figure 5B:
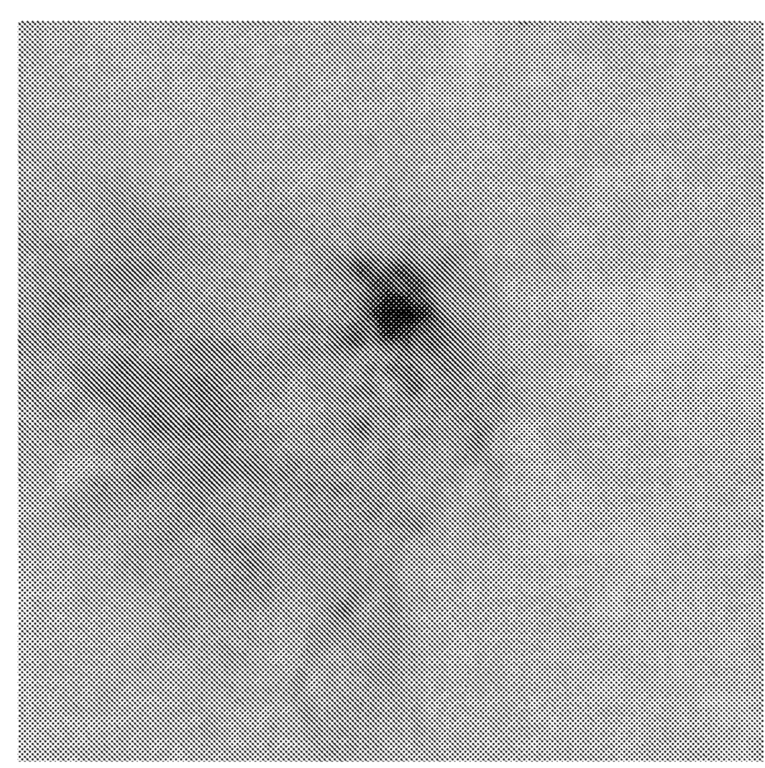
Figure 5C:
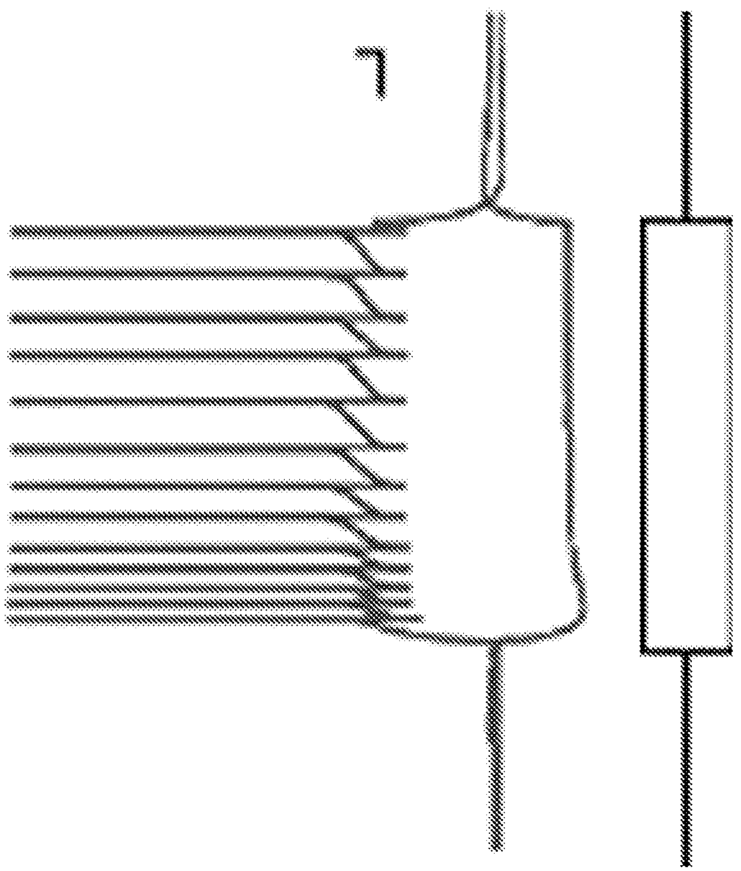
Figure 5C:
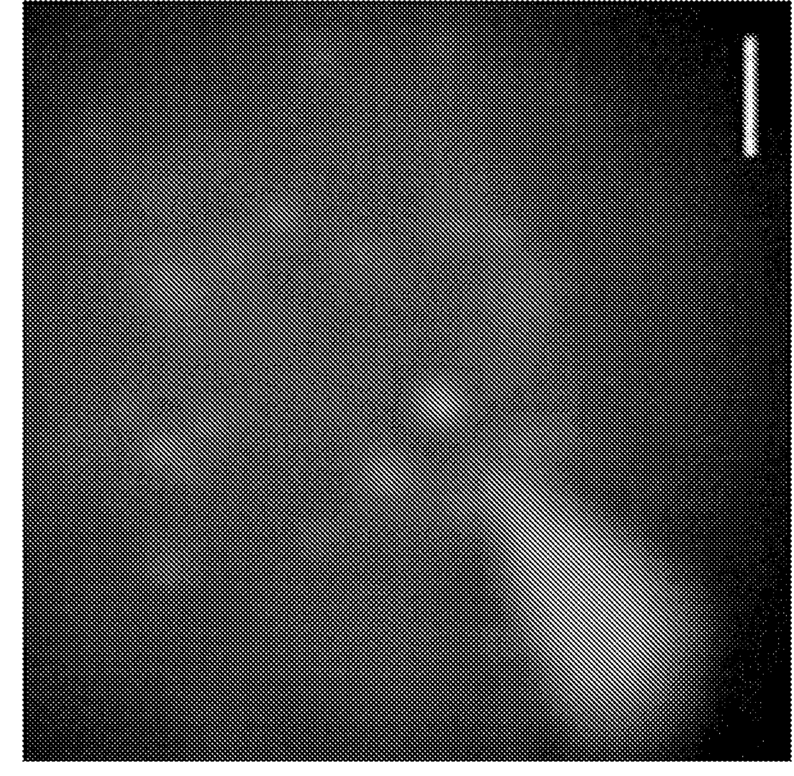
Figure 5C:
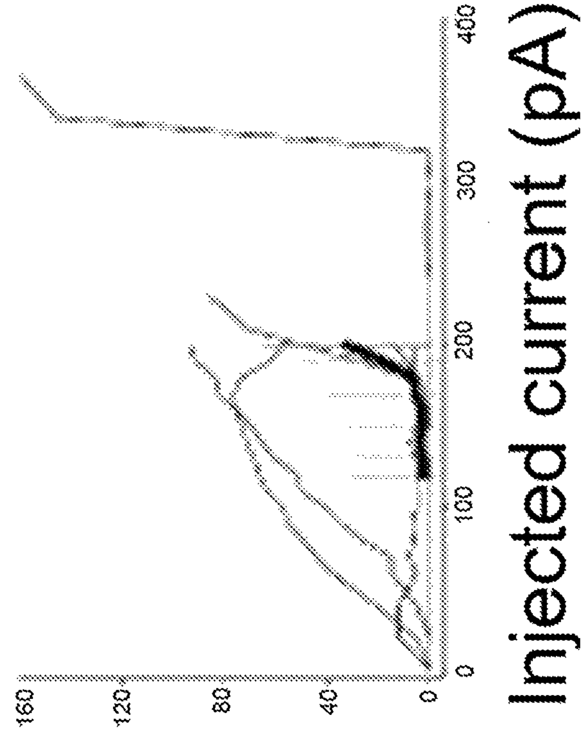
Figure 5C:
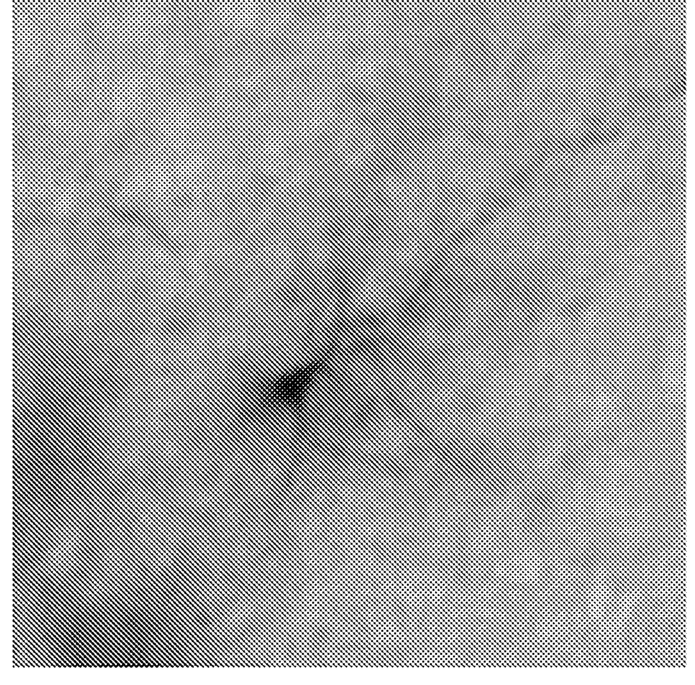
Figure 5D:
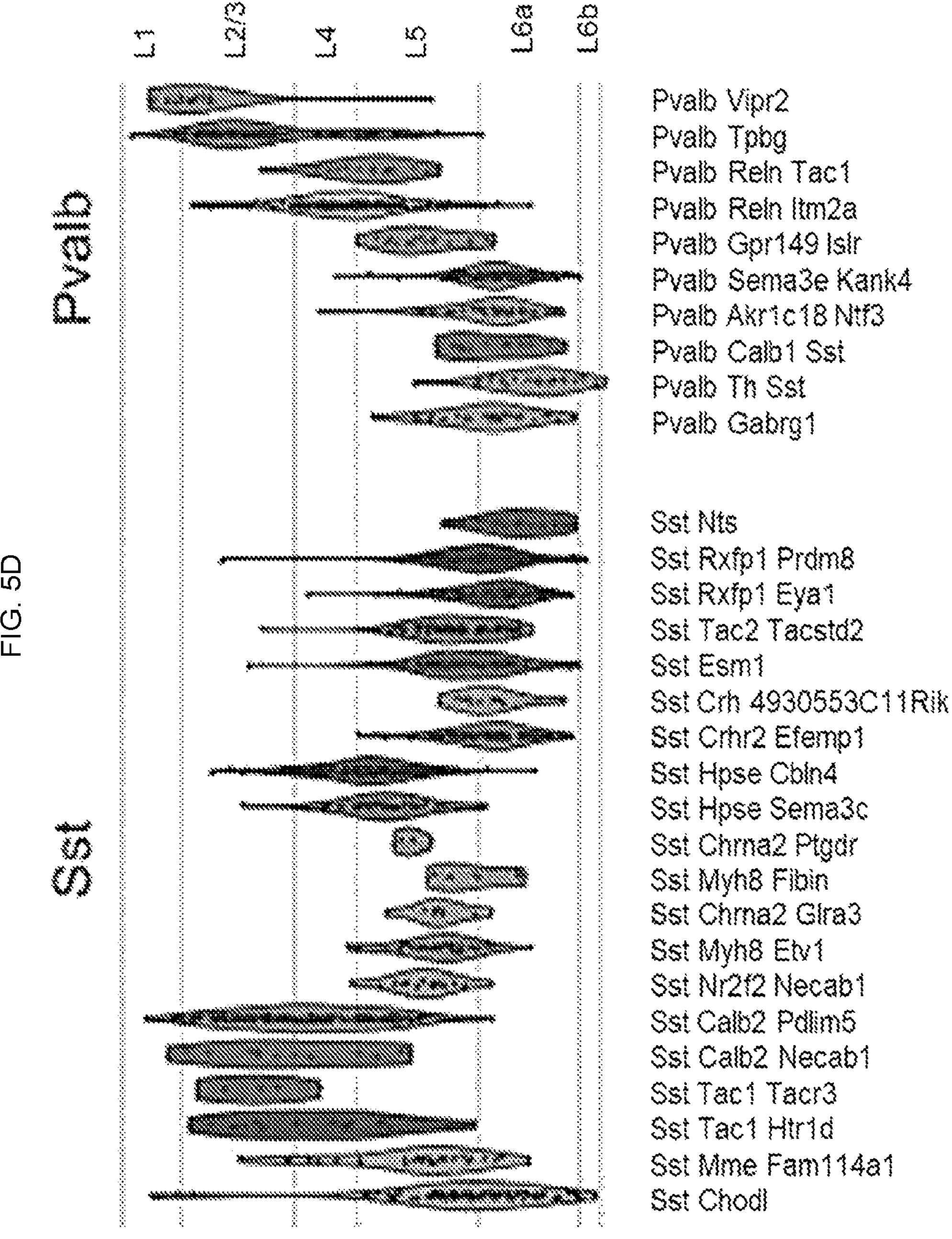

Cell-type class identification in vitro: In work with mice, three broad cell types, excitatory pyramidal cells, and two inhibitory types, the parvalbumin (Pvalb)- and somatostatin (SST)-expressing cells were the focus of this analysis (FIGS. 5A-5C). The analysis also focused in two brain areas, mouse primary visual cortex (V1) and the hippocampal CA1 region. Excitatory pyramidal cells were initially identified in transgenic mice with fluorescent reporters for layer 5 excitatory neurons (in V1) or by their pyramidal morphology, and then confirmed by their regular-spiking firing pattern (in response to intracellularly injected current steps) in patch-clamp recordings. Inhibitory Pvalb and SST cells were identified using Cre- or Flp-dependent transgenic mice with fluorescent reporters and confirmed by their fast-spiking firing pattern. The recorded cells were filled with biocytin, for post-hoc processing to reveal their cellular morphology. Patch-seq experiments which involve the single-cell RNA sequencing of electrophysiologically and morphologically recorded cells can also be performed to further refine the cell type identity through their transcriptomic profile as described in Tasic, B. et al. Nature 563, 72-78 (2018); (FIG. 5D; Gouwens, biorxiv.org/lookup/doi/10.1101/2020.02.03.932244 (2020)).

Cell-type-specific response to extracellular ES in vitro: The effects of extracellular ES while recording from a patch-clamped neuron at various membrane potentials—the neuron at rest, polarized (hyperpolarized or depolarized) potentials (FIGS. 6A, 6B), and at suprathreshold (spiking) potentials (FIGS. 7A-8F) was examined.

Recordations of voltages were simultaneously taken both inside the patched neuron and extracellularly at varying distances between the ES electrode and the patched soma (FIGS. 3A, 3B). The use of the multipatch system uniquely allowed assessment of the ES effects at the single compartment (soma) and membrane level, i.e. on the resulting extracellular voltage (Ve), intracellular somatic voltage (Vi), and the resulting membrane voltage (Vm, calculated as Vm=Vi−Ve) in the immediate vicinity of the patched soma.

ES entrainment of subthreshold cellular dynamics: Recordations were first taken from cells that were held at resting potential, while delivering ES of varying amplitude (25-200 nA) and frequency (1-100 Hz). For all cell types tested (pyramidal, Pvalb, SST), Vm is entrained to the extracellular ES and, importantly, ES entrainment is sustained beyond 100 Hz without any sign of membrane filtering, neither in terms of resulting Vm-amplitude and Vm-phase (FIGS. 6A, 6B). Moreover, across cell types, the subthreshold ES-induced Vm-oscillations follow Ve at 1800 phase (i.e. anti-phase). Excitatory and inhibitory cell classes in cortex (and, in fact, CA1; data not shown) follow ES unperturbed, from low to high frequencies, without any membrane filtering.

Figure 8A:
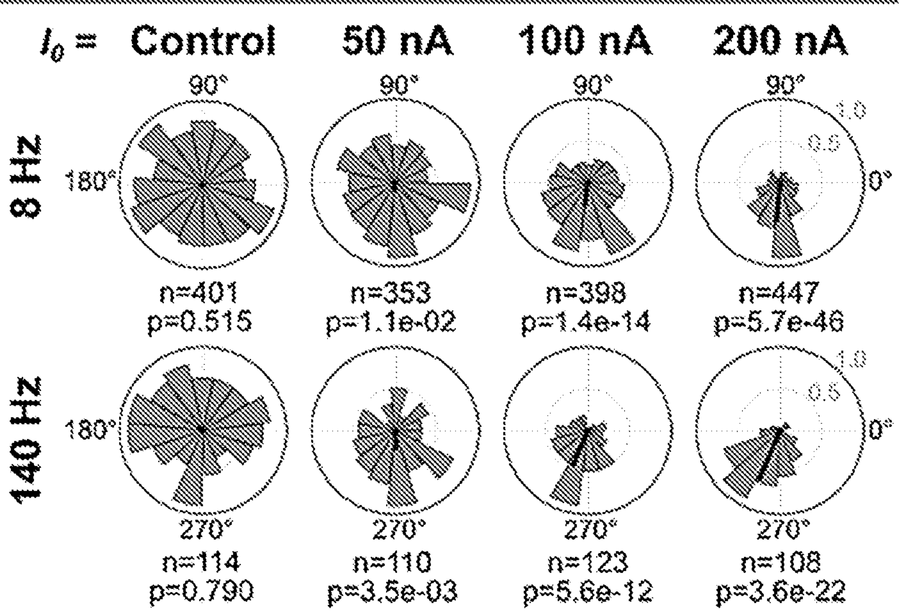
Figure 8B:
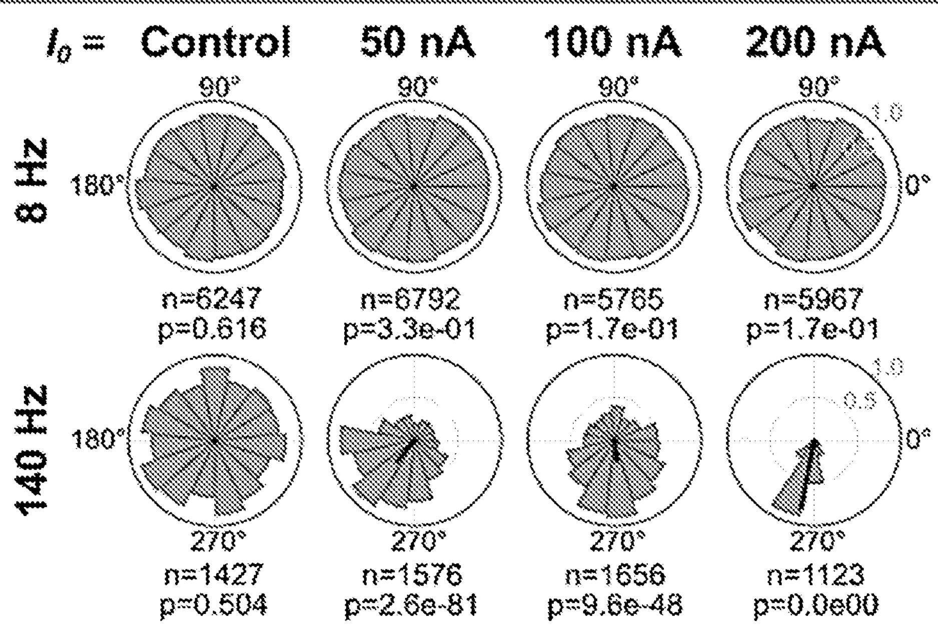

ES entrainment of spike-timing properties: The effect of ES on the spike-timing properties of excitatory and inhibitory cells of the cortex and hippocampus was next examined. This study focused on temporal entrainment of spiking during ES delivery. To do so, an intracellular DC current was first injected into neurons to elicit action potentials during a 9 second intracellular stimulation protocol, without applying any ES. In the next step, the same intracellular current was injected while concurrently applying ES at varying frequencies (1, 4, 8, 30, 120/140 Hz) and amplitudes (25 to 200 nA) (FIGS. 7A, 7B). Notably, the applied ES amplitudes did not alter the mean spike frequency (FIGS. 8A-8F, Control) which are driven by the intracellular current injection (extracellular ES alone does not elicit spiking; FIGS. 6A, 6B), i.e. the ES regime left their overall excitability unaffected. To analyze the impact of ES on the temporal structure of spiking, spike times during the ES was examined via circular statistics (with the ES-modulated Ve as reference; FIGS. 7A, 7B). Population-vector analysis was then used to examine whether spikes exhibit a phase preference to the imposed Ve, and the Rayleigh test was used to assess the uniformity of spike-phase distribution (null hypothesis: distribution is uniform). Anastassiou, et al., Nat Neurosci 14, 217-223 (2011). The spike distribution during control (i.e. no ES) was examined during alignment to a "virtual" extracellular field and compared to the spike distribution of neurons during ES. For cortical pyramidal cells, entrainment of spikes to ES results in an increasingly inhomogeneous spike phase distribution (measured in the decreasing p-values of the Rayleigh test) and increased population vector length as their spikes become increasingly entrained to specific Ve-phases (FIG. 8A).

Figure 8C:
Figure 8C:
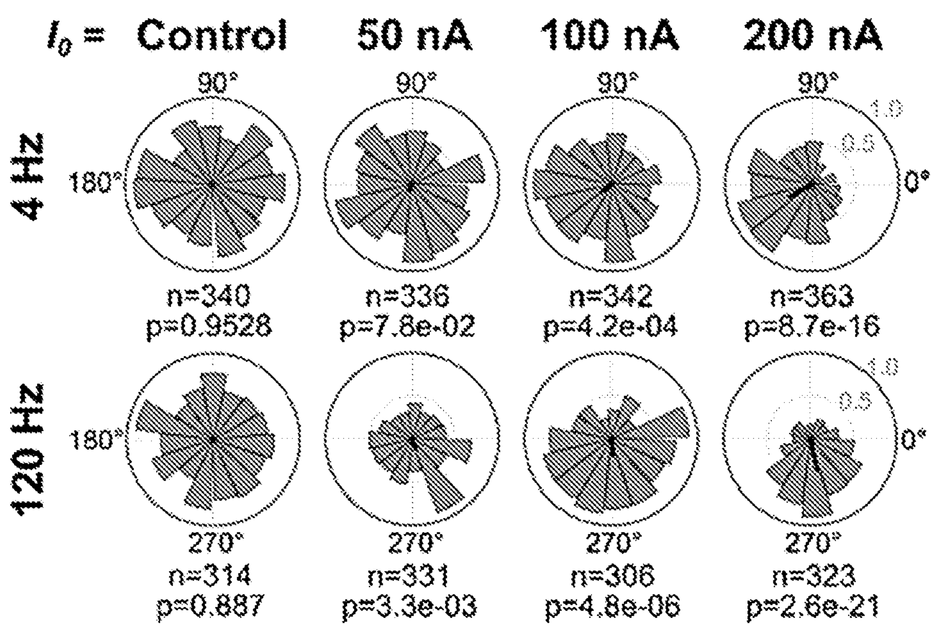
Figure 8D:
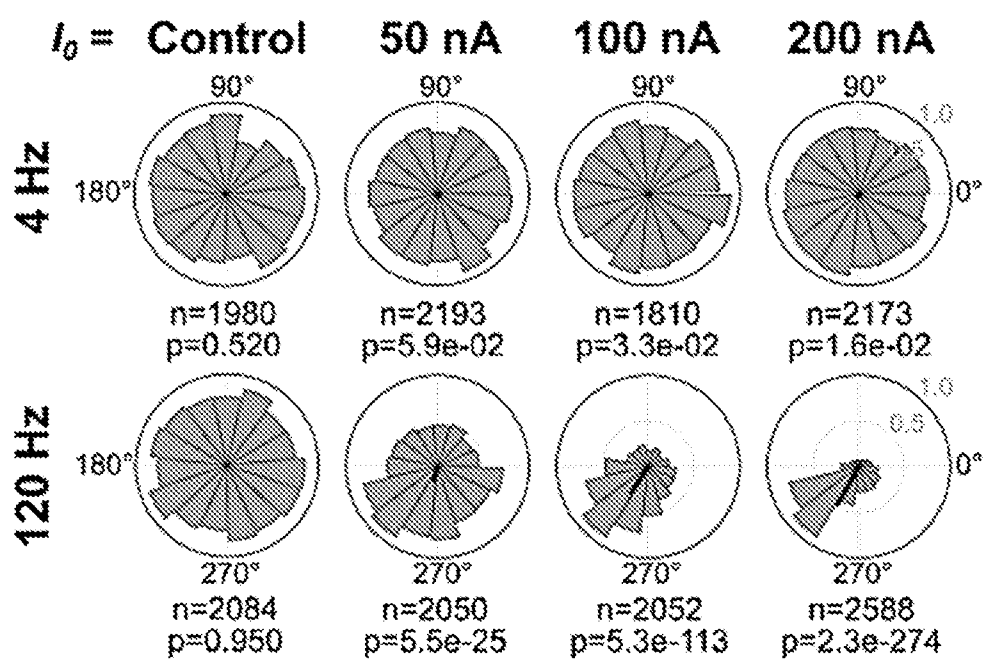
Figure 8E:
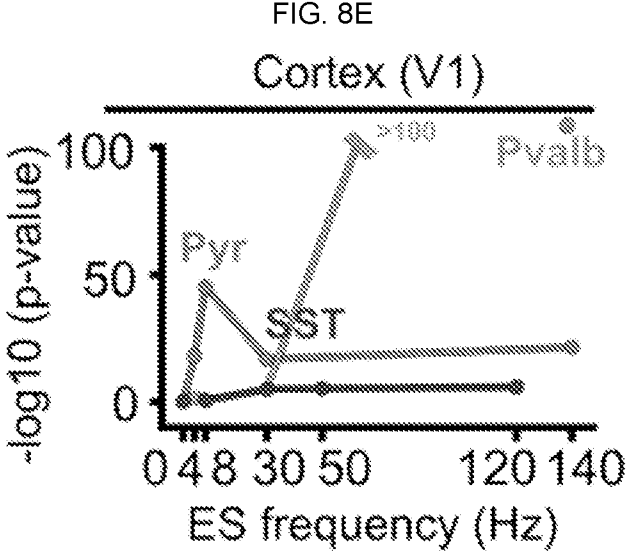
Figure 8F:
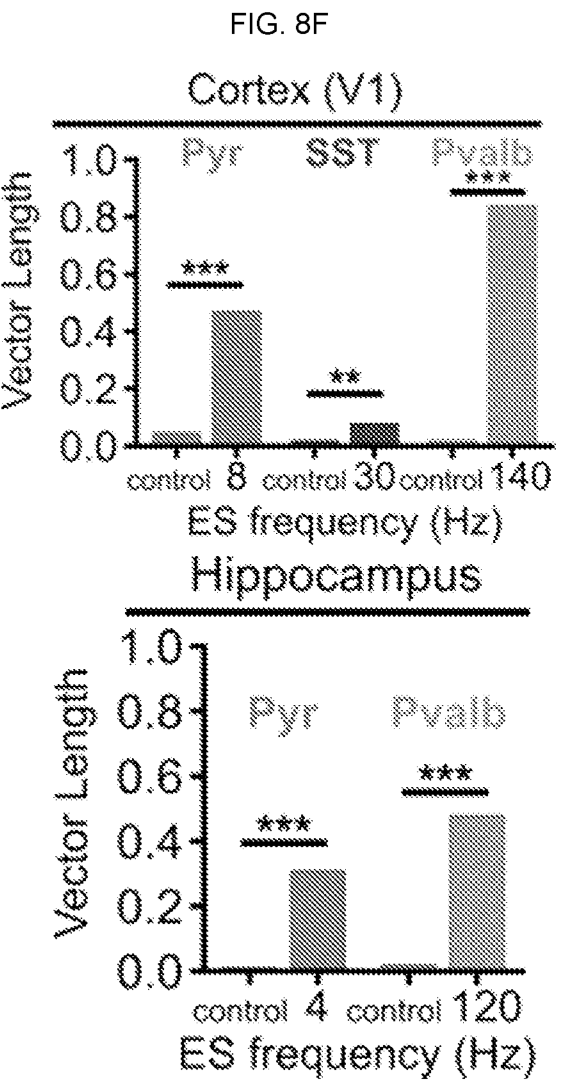

An important outcome of these experiments is the cell-type-specificity observed in the ES entrainment of spiking activity between excitatory and inhibitory cell types but also between the two inhibitory types. In neocortical excitatory cells, spiking entrainment to ES is particularly strong at lower ES frequencies (8 Hz; FIG. 8E) and increases with increasing ES amplitude (FIG. 8A) even if ES cannot elicit spiking in the absence of the intracellular DC stimulus (FIGS. 6A, 6B). On the other hand, in hippocampal pyramidal cells, entrainment to the extracellular ES is strong for 4 Hz and 120 Hz compared to other ES frequencies (FIG. 8C).

Conversely, neocortical and hippocampal inhibitory Pvalb cells exhibit extremely weak to no entrainment (assessed by the much higher p-values and smaller population vector length), at lower (<30 Hz) ES frequencies compared to pyramidal neurons. In fact, ES strongly entrains the intracellularly-induced Pvalb spiking activity for ES frequencies higher than 100 Hz. Even for weak ES amplitudes, in both neocortex and hippocampus, Pvalb display a very strong phase preference and non-uniformity in their spike-phase distribution for fast ES frequencies. Interestingly, SST interneurons exhibit preferential entrainment for intermediate ES frequencies, i.e. 30-60 Hz. Spike-phase entrainment can be clearly attributed to the ES as in the absence of ES, both excitatory (pyramidal) and inhibitory (Pvalb, SST) spiking displays uniform spike-phase distribution, i.e. complete lack of entrainment. Thus, in the presence of subthreshold ES (i.e. for ES-amplitudes that do not induce cellular spiking on their own), the intracellularly-induced spikes exhibit preference for firing at specific phases of the sinusoidal ES, with cell-type-specificity, and with the ES frequency being the critical parameter (FIGS. 8A-8F).

Figure 9A:
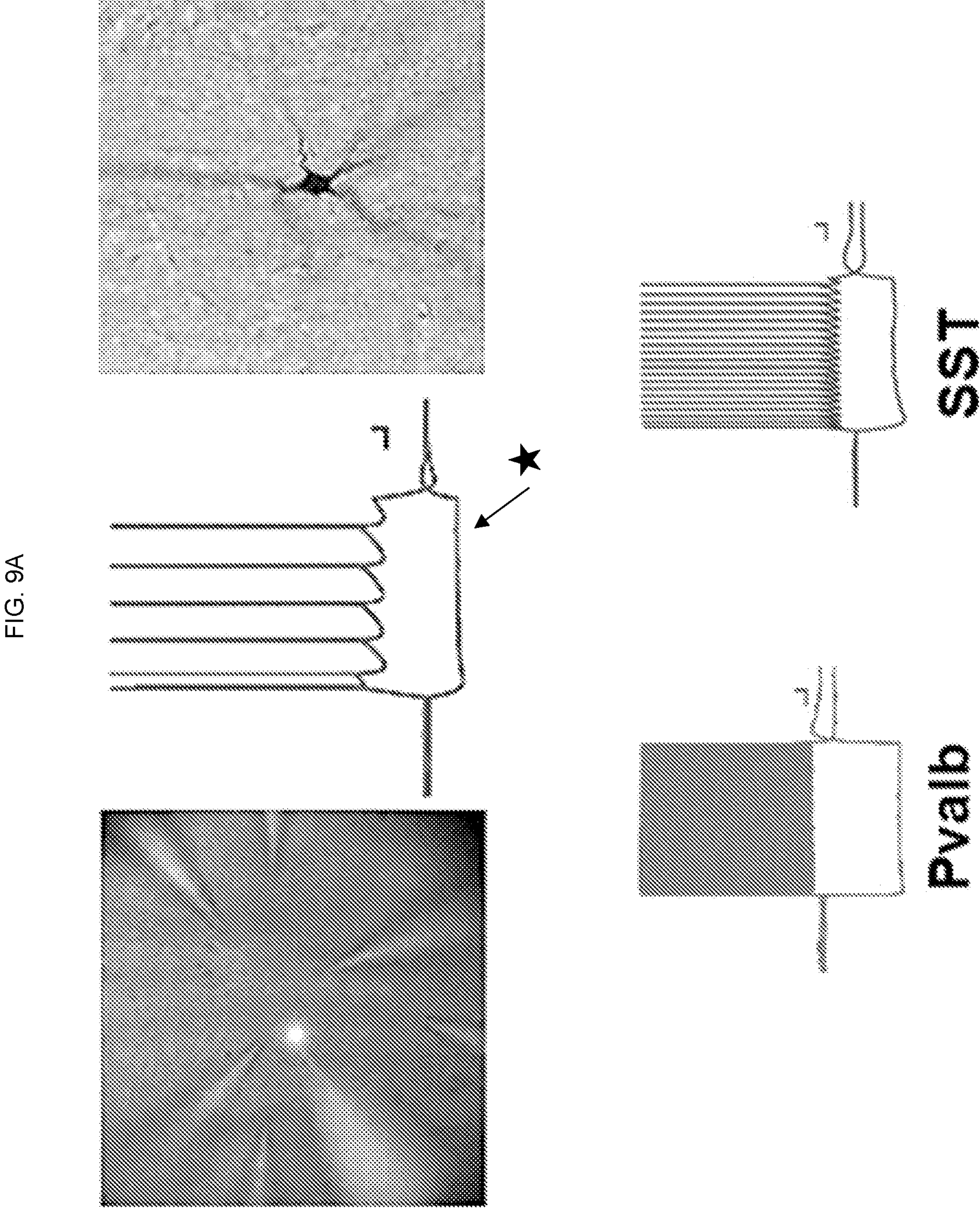
Figure 9B:
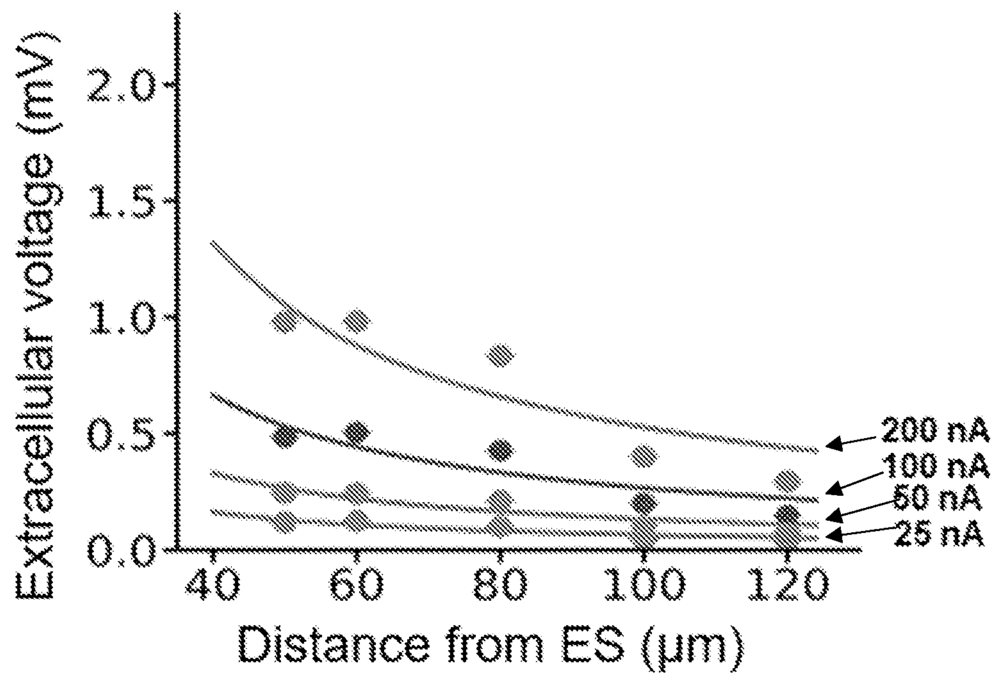
Figure 9C:
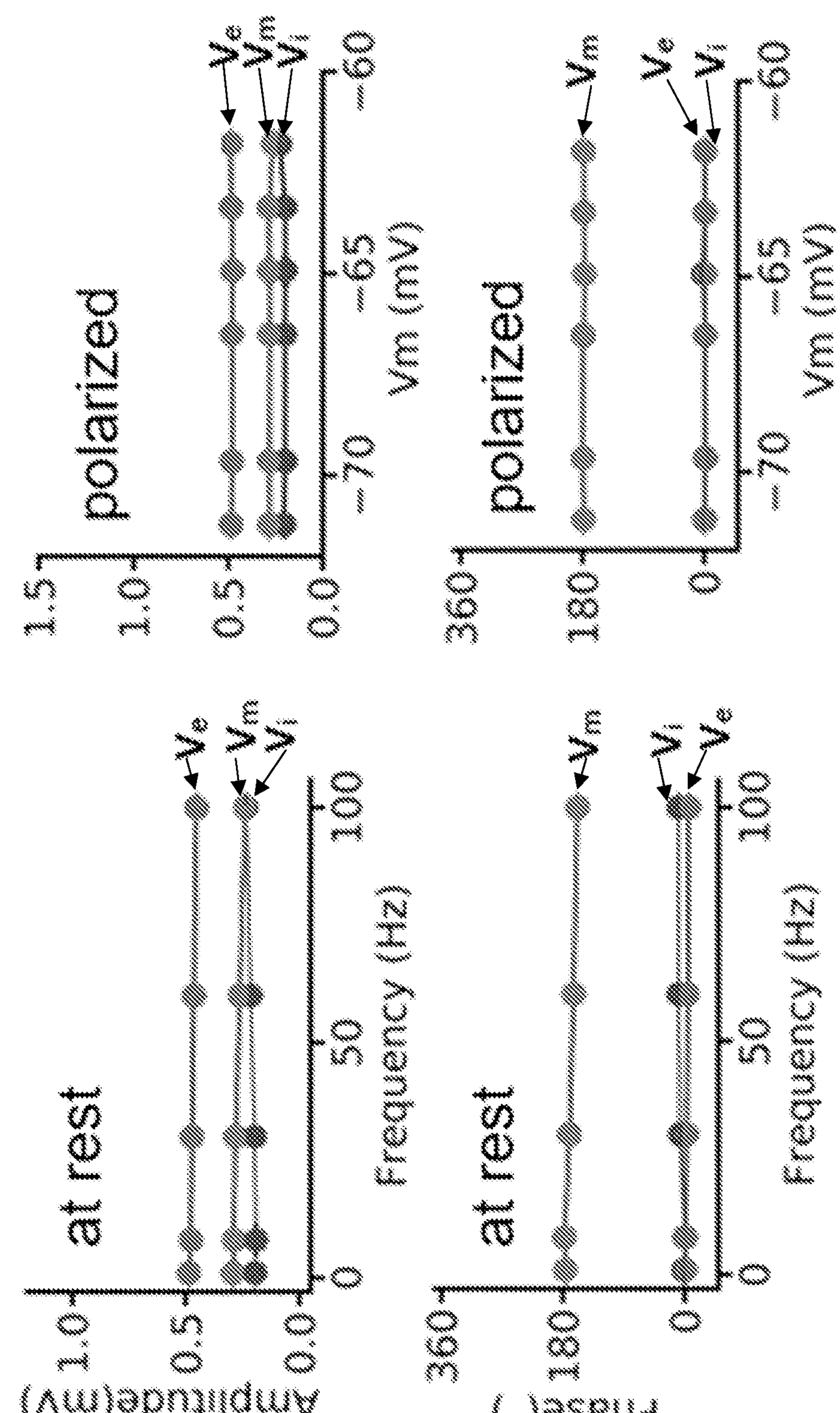
Figure 9D:
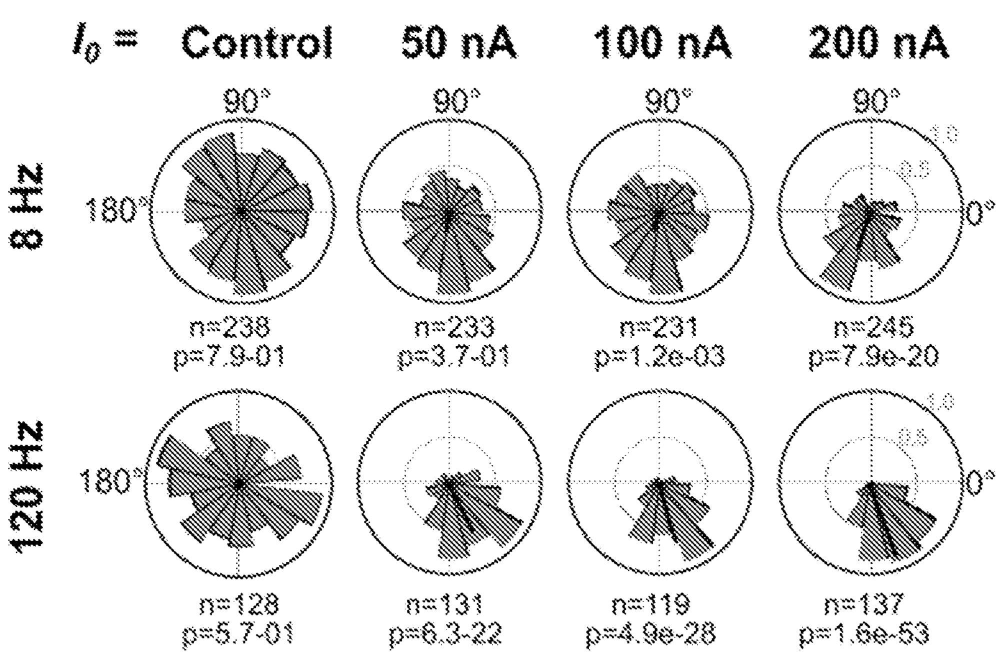
Figure 9D:
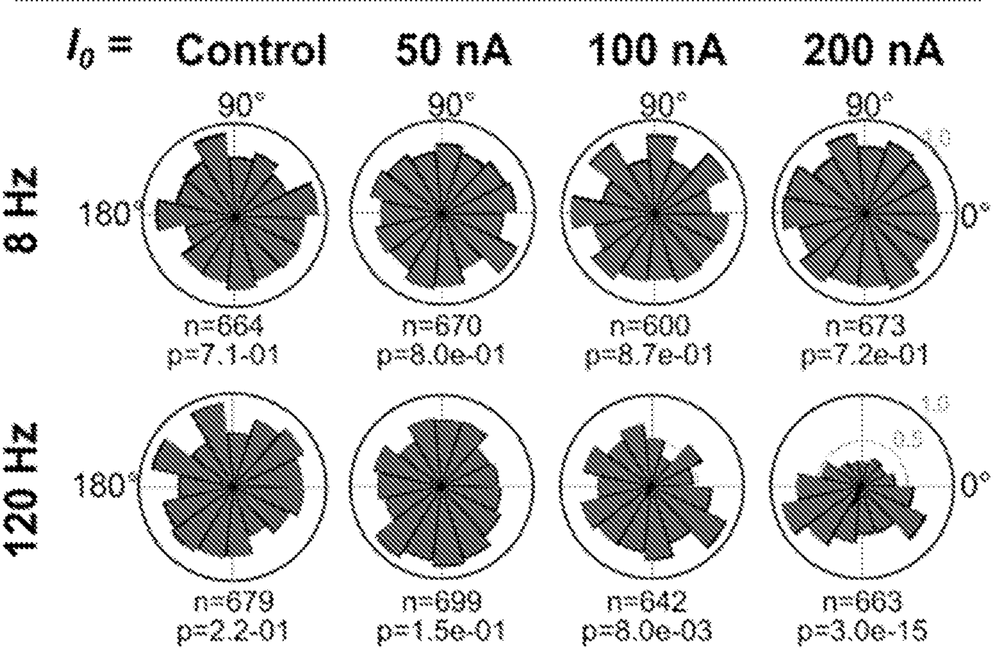

ES entrainment of human single neurons: Different human cell types were identified based on their electrophysiology (e.g. a regular spiking pyramidal cell, a fast-spiking Pvalb with less hyperpolarizing h-current sag vs. a fast-spiking SST with a more prominent hyperpolarizing sag; FIG. 9A). The effects of sinusoidal ES on a human pyramidal neuron from medial temporal lobe, using the same parameters as described in relation to the rodent experiments (FIGS. 6A-8F) are shown. At the subthreshold (at rest and polarized) levels, the human pyramidal neuron exhibits the same ability in following the ES, with similar strength and properties. This data with human neurons confirms the ability to similarly entrain human neurons with weak fields. Importantly, the cell-type-specific differences in the entrainment of spiking activity between excitatory (Pyramidal) and inhibitory (Fast-Spiking) cell types that were seen in the rodent experiments, and also manifested in the human neuron types as well.

(v) Closing Paragraphs. In certain examples, a waveform refers to the amplitude versus time relationship for an electrical signal, and may encompass one or more periods of a given signal. A sine wave describes a continuous and smooth periodic oscillation, as is well understood by those of ordinary skill in the art.

The techniques described in this disclosure can be implemented, at least in part, in hardware, software, firmware or any combination thereof. For example, various aspects of the techniques can be implemented within one or more microprocessors, DSPs, ASICs, FPGAs, or any other equivalent integrated or discrete logic circuitry, as well as any combinations of such components, embodied in programmers, such as physician or patient programmers, stimulators, or other devices. The term "processor" or "processing circuitry" can generally refer to any of the foregoing logic circuitry, alone or in combination with other logic circuitry, or any other equivalent circuitry.

Such hardware, software, and firmware can be implemented within the same device or within separate devices to support the various operations and functions described in this disclosure. In addition, any of the described units, modules or components can be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units can be performed by separate hardware or software components or integrated within common or separate hardware or software components.

When implemented in software, the functionality ascribed to the systems and devices described in this disclosure can be embodied as instructions on a computer-readable medium such as RAM, ROM, NVRAM, EEPROM, FLASH memory, magnetic media, optical media, or the like. The instructions can be executed to support one or more aspects of the functionality described in this disclosure.

If implemented in software, the techniques described in this disclosure can be stored on or transmitted over as one or more instructions or code on a computer-readable medium. Computer-readable media can include non-transitory computer storage media or communication media including any medium that facilitates transfer of a computer program from one place to another. Data storage media can be any available media that can be accessed by one or more computers or one or more processors to retrieve instructions, code and/or data structures for implementation of the techniques described in this disclosure. By way of example, and not limitation, such data storage media can comprise RAM, ROM, EEPROM, CD-ROM or other optical disk storage, magnetic disk storage, or other magnetic storage devices, flash memory, or any other medium that can be used to store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

The code can be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein can refer to any of the foregoing structure or any other structure suitable for implementation of the techniques described herein. Also, the techniques could be fully implemented in one or more circuits or logic elements.

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means has, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a statistically significant reduction in the ability to obtain a claimed effect according to a relevant experimental method described in the current disclosure.

Unless otherwise indicated, all numbers expressing quantities, properties such as frequency, amplitude, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value, including values between whole integers and all real numbers.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the examples or when application of the meaning renders any construction meaningless or essentially meaningless. In cases where the construction of the term would render it meaningless or essentially meaningless, the definition should be taken from Webster's Dictionary, 3rd Edition or a reference well-known to those of ordinary skill in the art, such as Principles of Neural Science, 5$^{th}$ Edition (Eds. Sydor & Lebowitz) The McGraw-Hill Companies, Inc. (2013) (MHID: 0-07-139011-1; ISBN: 978-0-07-139011-8).

What is claimed is:

1. A method comprising delivering electrical stimulation (ES) at a first frequency and a second frequency to a brain of a subject wherein the ES having the first frequency entrains a first selected cell type and the ES having the second frequency entrain a second selected cell type, and wherein the first frequency is greater than zero and less than 30 Hertz (Hz) and the first selected cell type is an excitatory neuron, and the second frequency is 30 Hz or greater and the second selected cell type is an inhibitory neuron.

2. The method of claim 1, wherein the first frequency is less than 12 Hz, and the excitatory neuron is an excitatory cortical neuron or an excitatory hippocampal neuron.

3. The method of claim 2, wherein the excitatory cortical neuron is within a primary visual cortex or the excitatory hippocampal neuron is within a CA1 region of a hippocampus.

4. The method of claim 1, wherein:

the first frequency is 8 Hz, and the excitatory neuron is a pyramidal neuron within the primary visual cortex, or the first frequency is 4 Hz and the excitatory neuron is a pyramidal neuron within the hippocampus.

5. The method of claim 1, wherein the subject is performing a task during the delivering.

6. The method of claim 1, wherein the delivering is through an implantable device comprising an ES generator or a non-invasive device comprising an ES generator.

7. The method of claim 1, wherein the delivering utilizes a sinusoidal waveform.

8. The method of claim 1, wherein the delivering utilizes a composite waveform carrying the first frequency and the second frequency.

9. The method of claim 8, wherein the delivering comprises producing a first signal having the first frequency and a second signal having the second frequency; and superimposing the first and second signals upon the brain of the subject in a manner that is not phase locked, wherein the superimposing entrains the first selected cell type and the second selected cell type within the brain of the subject.

10. The method of claim 9, wherein the first and second selected cell types include excitatory neurons and inhibitory neurons; cortical neurons and hippocampal neurons; pyramidal neurons and Pvalb neurons; pyramidal neurons and Sst neurons; and/or Pvalb neurons and Sst neurons.

11. The method of claim 9, wherein:

the first frequency is from greater than 0 to 12 Hz and the second frequency is from 30 to 60 Hz;

the first frequency is from greater than 0 to 12 Hz and the second frequency is from 100 Hz to 160 Hz;

the first frequency is from greater than 0 to 12 Hz and the second frequency is 30 Hz;

the first frequency is from greater than 0 to 12 Hz and the second frequency is 50 Hz;

the first frequency is from greater than 0 to 12 Hz and the second frequency is 60 Hz;

the first frequency is from greater than 0 to 12 Hz and the second frequency is 100 Hz;

the first frequency is from greater than 0 to 12 Hz and the second frequency is 120 Hz;

the first frequency is from greater than 0 to 12 Hz and the second frequency is 140 Hz;

the first frequency is 4 Hz and the second frequency is 30 or greater;

the first frequency is 4 Hz and the second frequency is 30 Hz;

the first frequency is 4 Hz and the second frequency is 50 Hz;

the first frequency is 4 Hz and the second frequency is 60 Hz;

the first frequency is 4 Hz and the second frequency is 100 Hz;

the first frequency is 4 Hz and the second frequency is 120 Hz;

the first frequency is 4 Hz and the second frequency is 140 Hz;

the first frequency is 8 Hz and the second frequency is 30 or greater;

the first frequency is 8 Hz and the second frequency is 30 Hz;

the first frequency is 8 Hz and the second frequency is 50 Hz;

the first frequency is 8 Hz and the second frequency is 60 Hz;

the first frequency is 8 Hz and the second frequency is 100 Hz;

the first frequency is 8 Hz and the second frequency is 120 Hz; or the first frequency is 8 Hz and the second frequency is 140 Hz.

12. The method of claim 8, wherein the delivering comprises (a) creating a first electric field between electrodes in a first pair of electrodes; and (b) creating a second electric field between electrodes in a second pair of electrodes, such that (i) the first and second electric fields constructively and destructively interfere with each other to create an amplitude-modulated waveform and (ii) a largest envelope amplitude of the amplitude-modulated waveform occurs in a cortical region and/or a hippocampal region of the brain of the subject; wherein, during steps (a) and (b), the first and second electrode pairs are electrically coupled to the brain.

13. The method of claim 12, wherein the amplitude-modulated waveform entrains selected neurons in the cortical region and/or the hippocampal region of the brain of the subject.

14. The method of claim 12, wherein the first and second electric fields are temporally asymmetric.

15. The method of claim 7, wherein the second frequency is greater than 100 Hz and the inhibitory neuron is a parvalbumin (Pvalb) neuron, or the second frequency is in a range of 30 Hz-60 Hz and the inhibitory neuron is a somatostatin (Sst) neuron.

16. The method of claim 15, wherein the inhibitory neuron is an inhibitory cortical neuron or an inhibitory hippocampal neuron.

17. The method of claim 16, wherein the inhibitory cortical neuron is within a primary visual cortex or the inhibitory hippocampal neuron is within a CA1 region of a hippocampus.

18. The method of claim 15, wherein the inhibitory neuron is a parvalbumin (Pvalb) neuron.

19. The method of claim 15, wherein the second frequency is 140 Hz and the inhibitory neuron is a Pvalb neuron within a primary visual cortex, or the second frequency is 120 Hz and the inhibitory neuron is a Pvalb neuron within a hippocampus.

20. A method comprising entraining excitatory pyramidal cortical neurons within a primary visual cortex while simultaneously entraining inhibitory cortical neurons within the primary visual cortex in a brain of a subject, the method comprising:

delivering electrical stimulation(ES) to the brain of the subject, wherein the ES comprises a first frequency and a second frequency, wherein the first frequency is greater than 0 Hz to 12 Hz and the second frequency is from 100-160 Hz, thereby entraining excitatory pyramidal cortical neurons within the primary visual cortex while simultaneously entraining inhibitory cortical neurons within the primary visual cortex in the subject.

* * * * *